US010738115B2

(12) United States Patent
Stanimirovic et al.

(10) Patent No.: US 10,738,115 B2
(45) Date of Patent: Aug. 11, 2020

(54) HUMANIZED ANTIBODIES TRANSMIGRATING THE BLOOD-BRAIN BARRIER AND USES THEREOF

(71) Applicant: National Research Council of Canada, Ottawa (CA)

(72) Inventors: Danica Stanimirovic, Ottawa (CA); Kristin Kemmerich, Ottawa (CA); Yves Durocher, Montréal (CA); Traian Sulea, Kirkland (CA)

(73) Assignee: National Research Council of Canada, Ottawa (CA)

(*) Notice: Subject to any disclaimer, the term of this patent is extended or adjusted under 35 U.S.C. 154(b) by 0 days.

(21) Appl. No.: 16/314,891

(22) PCT Filed: Jul. 4, 2017

(86) PCT No.: PCT/IB2017/054036
§ 371 (c)(1),
(2) Date: Jan. 3, 2019

(87) PCT Pub. No.: WO2018/007950
PCT Pub. Date: Jan. 11, 2018

(65) Prior Publication Data

US 2019/0241653 A1 Aug. 8, 2019

Related U.S. Application Data

(60) Provisional application No. 62/358,777, filed on Jul. 6, 2016.

(51) Int. Cl.
*C07K 16/28* (2006.01)
*A61K 47/68* (2017.01)

(52) U.S. Cl.
CPC .......... *C07K 16/28* (2013.01); *A61K 47/6849* (2017.08); *C07K 2317/22* (2013.01); *C07K 2317/24* (2013.01); *C07K 2317/35* (2013.01); *C07K 2317/52* (2013.01); *C07K 2317/565* (2013.01); *C07K 2317/567* (2013.01); *C07K 2317/569* (2013.01); *C07K 2317/64* (2013.01); *C07K 2317/70* (2013.01); *C07K 2317/94* (2013.01); *C07K 2319/30* (2013.01)

(58) Field of Classification Search
CPC .......... C07K 2317/24; C07K 2317/565; C07K 2317/567; C07K 2317/52; C07K 16/28; C07K 2317/94; C07K 2317/64; C07K 2317/35; C07K 2317/22; C07K 2317/70; C07K 2319/30; A61K 47/6849
See application file for complete search history.

(56) References Cited

FOREIGN PATENT DOCUMENTS

| | | | |
|---|---|---|---|
| WO | WO 1995/004069 A1 | | 2/1995 |
| WO | WO 2002/057445 A1 | | 7/2002 |
| WO | WO 2003/046560 A2 | | 6/2003 |
| WO | WO 2004/076670 A1 | | 9/2004 |
| WO | WO 2007/036021 A1 | | 4/2007 |
| WO | WO 2011/127580 A1 | | 10/2011 |
| WO | WO 2013/106577 A2 | * | 7/2013 |

OTHER PUBLICATIONS

Abbott et al., Blood-brain barrier structure and function and the challenges for CNS drug delivery. J Inherit Metab Dis. May 2013;36(3):437-49. doi: 10.1007/s10545-013-9608-0. Epub Apr. 23, 2013.
Abulrob et al., The blood-brain barrier transmigrating single domain antibody: mechanisms of transport and antigenic epitopes in human brain endothelial cells. J Neurochem. Nov. 2005;95(4):1201-14.
Arbabi Ghahroudi et al., Selection and identification of single domain antibody fragments from camel heavy-chain antibodies. FEBS Lett. Sep. 15, 1997;414(3):521-6.
Bell et al., Differential tumor-targeting abilities of three single-domain antibody formats. Cancer Lett. Mar. 1, 2010;289(1):81-90. doi: 10.1016/j.canlet.2009.08.003. Epub Aug. 28, 2009.
Chothia et al., Canonical structures for the hypervariable regions of immunoglobulins. J Mol Biol. Aug. 20, 1987;196(4):901-17.
Davies et al., Affinity improvement of single antibody VH domains: residues in all three hypervariable regions affect antigen binding. Immunotechnology. Sep. 1996;2(3):169-79.
De Kruif et al., Leucine zipper dimerized bivalent and bispecific scFv antibodies from a semi-synthetic antibody phage display library. J Biol Chem. Mar. 29, 1996;271(13):7630-4.
Demeule et al., Involvement of the low-density lipoprotein receptor-related protein in the transcytosis of the brain delivery vector angiopep-2. J Neurochem. Aug. 2008;106(4):1534-44. doi: 10.1111/j.1471-4159.2008.05492.x. Epub May 19, 2008.
Dumoulin et al., Single-domain antibody fragments with high conformational stability. Protein Sci. Mar. 2002;11(3):500-15.
Eisenberg et al., Analysis of membrane and surface protein sequences with the hydrophobic moment plot. J Mol Biol. Oct. 15, 1984;179(1):125-42.
Erdlenbruch et al., Alkylglycerol opening of the blood-brain barrier to small and large fluorescence markers in normal and C6 glioma-bearing rats and isolated rat brain capillaries. Br J Pharmacol. Dec. 2003;140(7):1201-10. Epub Nov. 3, 2003.
Gan et al., Gene delivery with viral vectors for cerebrovascular diseases. Front Biosci (Elite Ed). Jan. 1, 2013; 5: 188-203. Epub Jan. 1, 3012.
Garberg et al., In vitro models for the blood-brain barrier. Toxicol In Vitro. Apr. 2005;19(3):299-334.

(Continued)

*Primary Examiner* — Gregory S Emch
(74) *Attorney, Agent, or Firm* — Wolf, Greenfield & Sacks, P.C.

(57) ABSTRACT

The present invention relates to antibodies and fragments thereof derived by humanization of an existing antibody, and methods of making them. The humanized antibodies of the present invention show enhanced binding to the brain endothelial antigen, improved transmigration across the blood-brain barrier, and increased thermal stability relative to the parent non-humanized antibody.

14 Claims, 6 Drawing Sheets

Specification includes a Sequence Listing.

(56) References Cited

OTHER PUBLICATIONS

Gergov et al., Simultaneous screening for 238 drugs in blood by liquid chromatography-ion spray tandem mass spectrometry with multiple-reaction monitoring. J Chromatogr B Analyt Technol Biomed Life Sci. Sep. 25, 2003;795(1):41-53.
Gonzales et al., Minimizing the immunogenicity of antibodies for clinical application. Tumour Biol. Jan.-Feb. 2005;26(1):31-43.
Gottesman et al., Biochemistry of multidrug resistance mediated by the multidrug transporter. Annu Rev Biochem. 1993;62:385-427.
Greenfield, Using circular dichroism collected as a function of temperature to determine the thermodynamics of protein unfolding and binding interactions. Nat Protoc. 2006;1(6):2527-35.
Guillaume et al., Intra-arterial chemotherapy with osmotic blood-brain barrier disruption for aggressive oligodendroglial tumors: results of a phase I study. Neurosurgery. Jan. 2010;66(1):48-58; discussion 58. doi: 10.1227/01.
Hamers-Casterman et al., Naturally occurring antibodies devoid of light chains. Nature. Jun. 3, 1993;363(6428):446-8.
Haqqani et al., Multiplexed evaluation of serum and CSF pharmacokinetics of brain-targeting single-domain antibodies using a NanoLC-SRM-ILIS method. Mol Pharm. May 6, 2013;10(5):1542-56. doi: 10.1021/mp3004995. Epub Dec 6, 2012.
Hussack et al., Engineered Single-Domain Antibodies with High Protease Resistance and Thermal Stability. PLoS One. Nov. 30, 2011;6(11):e28218. https://doi.org/10.1371/journal.pone.0028218.
Hussack et al., Neutralization of Clostridium difficile toxin A with single-domain antibodies targeting the cell receptor binding domain. J Biol Chem. Mar. 18, 2011;286(11):8961-76. doi: 10.1074/jbc.M110.198754. Epub Jan. 7, 2011.
Iqbal et al., Kinetic analysis of novel mono- and multivalent VHH-fragments and their application for molecular imaging of brain tumours. Br J Pharmacol. Jun. 2010; 160(4): 1016-1028. doi: 10.1111/j.1476-5381.2010.00742.x.
Jespers et al., Aggregation-resistant domain antibodies selected on phage by heat denaturation. Nat Biotechnol. Sep. 2004;22(9):1161-5. Epub Aug. 8, 2004.
Jones et al., Replacing the complementarity-determining regions in a human antibody with those from a mouse. Nature. May 29-Jun. 4, 1986;321(6069):522-5.
Kabat et al., Identical V region amino acid sequences and segments of sequences in antibodies of different specificities. Relative contributions of VH and VL genes, minigenes, and complementarity-determining regions to binding of antibody-combining sites. J Immunol. Sep. 1, 1991;147(5):1709-19.
Kim et al., Disulfide linkage engineering for improving biophysical properties of human VH domains. Protein Eng Des Sel. Oct. 2012;25(10):581-9. Epub Aug. 30, 2012.
Li et al., Pentabody-mediated antigen delivery induces antigen-specific mucosal immune response. Mol Immunol. May 2009;46(8-9):1718-26. doi: 10.1016/j.molimm.2009.02.007. Epub Mar. 9, 2009.
Merritt et al., AB5 toxins. Curr Opin Struct Biol. Apr. 1995;5(2):165-71.
Muruganandam et al., Selection of phage-displayed llama single-domain antibodies that transmigrate across human blood-brain barrier endothelium. Faseb J. Feb. 2002;16(2):240-2. Epub Dec. 28, 2001.
Nhan et al., Drug delivery to the brain by focused ultrasound induced blood-brain barrier disruption: quantitative evaluation of enhanced permeability of cerebral vasculature using two-photon microscopy. J Control Release. Nov. 28, 2013;172(1):274-280. doi: 10.1016/j jconrel.2013.08.029. Epub Sep. 2, 2013.
Nicaise et al., Affinity transfer by CDR grafting on a nonimmunoglobulin scaffold. Protein Sci. Jul. 2004; 13(7): 1882-1891. doi: 10.1110/ps.03540504.
Nielsen et al., Targeting of Bivalent Anti-ErbB2 Diabody Antibody Fragments to Tumor Cells Is Independent of the Intrinsic Antibody Affinity. Cancer Research. Nov. 15, 2000;60:6434-40.
Nuttall et al., Isolation and characterization of an IgNAR variable domain specific for the human mitochondrial translocase receptor Tom70. Eur J Biochem. Sep. 2003;270(17):3543-54.
Pardridge, Drug and gene delivery to the brain: the vascular route. Neuron. Nov. 14, 2022;36(4):555-8.
Pardridge, Transport of small molecules through the blood-brain barrier: biology and methodology. Advanced Drug Delivery Reviews. Jul. 1995;15(1-3):5-36. https://doi.org/10.1016/0169-409X(95)00003-P.
Pardridge et al., Selective transport of an anti-transferrin receptor antibody through the blood-brain barrier in vivo. J Pharmacol Exp Ther. Oct. 1991;259(1):66-70.
Preston et al., Graded reversible opening of the rat blood-brain barrier by intracarotid infusion of sodium caprate. J Neurosci Methods. Mar. 15, 2008;168(2):443-9. Epub Nov. 19, 2007.
Queen et al., A humanized antibody that binds to the interleukin 2 receptor. Proc Natl Acad Sci U S A. Dec. 1989; 86(24): 10029-10033. doi: 10.1073/pnas.86.24.10029.
Ridgway et al., 'Knobs-into-holes' engineering of antibody CH3 domains for heavy chain heterodimerization. PEDS. Jul. 1, 1996;9(7):617-21. https://doi.org/10.1093/protein/9.7.617.
Riechmann et al., Reshaping human antibodies for therapy. Nature. Mar. 24, 1988;332(6162):323-7.
Samuels et al., Modulation of vinblastine resistance with cyclosporine: A phase I study. Clinical Pharmacology and Therapeutics. Oct. 14, 1993;54:421-9; doi:10.1038/elpt.1993.169.
Spreter Von Kreudenstein et al., Protein engineering and the use of molecular modeling and simulation: the case of heterodimeric Fc engineering. Methods. Jan. 1, 2014;65(1):77-94. doi: 10.1016/j.ymeth.2013.10.016.
Sumbria et al., Pharmacokinetics and brain uptake of an IgG-TNF decoy receptor fusion protein following intravenous, intraperitoneal, and subcutaneous administration in mice. Mol Pharm. Apr. 1, 2013;10(4):1425-31. doi: 10.1021/mp400004a. Epub Feb. 28, 2013.
Tempest et al., Reshaping a Human Monoclonal Antibody to Inhibit Human Respiratory Syncytial Virus Infection in Vivo. Nature Biotechnol. Mar. 1, 1991;9:266-71.
To et al., Isolation of monomeric human V(H)s by a phage selection. J Biol Chem. Dec. 16, 2005;280(50):41395-403. Epub Oct. 12. 2005.
Tsurushita et al., Design of humanized antibodies: from anti-Tac to Zenapax. Methods. May 2005;36(1):69-83.
Watanabe et al., Comparative Study on Reversal Efficacy of SDZ PSC 833, Cyclosporin a and Verapamil on Multidrug Resistance in vitro and in vivo. Acta Oncologica. Jul. 8, 1995;34(2):235-41. https://doi.org/10.3109/02841869509093961.
Xiao et al., Receptor-Mediated Endocytosis and Brain Delivery of Therapeutic Biologics. Int J Cell Biol. doi: 10.1155/2013/703545. Epub Jun. 11, 2013.
Yaksh et al., Chronic catheterization of the spinal subarachnoid space. Physiol Behav. Dec. 1976;17(6):1031-6.
Yu et al., Boosting brain uptake of a therapeutic antibody by reducing its affinity for a transcytosis target. Sci Transl Med. May 25, 2011;3(84):84ra44. doi: 10.1126/scitranslmed.3002230.
Zhu et al., Combody: one-domain antibody multimer with improved avidity. Immunology and Cell Biology. 2010;88(6):667-75.
Zuchero et al., Discovery of Novel Blood-Brain Barrier Targets to Enhance Brain Uptake of Therapeutic Antibodies. Neuron. Jan. 6, 2016;89(1):70-82. doi: 10.1016/j.neuron.2015.11.024. Epub Dec. 10, 2015.
PCT/IB2017/054036, Oct. 12, 2017, International Search Report and Written Opinion.
PCT/IB2017/054036, Jan. 17, 2019, International Preliminary Report on Patentability.

* cited by examiner

| | | |
|---|---|---|
| FC5 | DVQLQASGGGLVQAGGSLRLSCAASGFKITHYTMGWFRQAPGKEREFVSRITWGG | |
| H1 | EVQLVESGGGLVQPGGSLRLSCAASGFKITHYTMGWVRQAPGKGLEWVSRITWGG | |
| H2 | EVQLVESGGGLVQPGGSLRLSCAASGFKITHYTMGWVRQAPGKGLEWVSRITWGG | |
| H3 | EVQLVESGGGLVQPGGSLRLSCAASGFKITHYTMGWFRQAPGKGLEFVSRITWGG | |
| H4 | DVQLVESGGGLVQPGGSLRLSCAASGFKITHYTMGWFRQAPGKGLEFVSRITWGG | |
| H5 | DVQLVESGGGLVQPGGSLRLSCAASGFKITHYTMGWFRQAPGKGREFVSRITWGG | |
| H6 | DVQLVESGGGLVQPGGSLRLSCAASGFKITHYTMGWFRQAPGKEREFVSRITWGG | |
| H7 | EVQLVESGGGLVQPGGSLRLSCAASGFKITHYTMGWFRQAPGKEREFVSRITWGG | |
| FC5 | DNTFYSNSVKGRFTISRDNAKNTVYLQMNSLKPEDTADYYCAAGSTSTATPLRVD | |
| H1 | DNTFYSNSVKGRFTISRDNSKNTLYLQMNSLRAEDTAVYYCAAGSTSTATPLRVD | |
| H2 | DNTFYSNSVKGRFTISRDNSKNTVYLQMNSLRAEDTAVYYCAAGSTSTATPLRVD | |
| H3 | DNTFYSNSVKGRFTISRDNSKNTVYLQMNSLRAEDTAVYYCAAGSTSTATPLRVD | |
| H4 | DNTFYSNSVKGRFTISRDNSKNTVYLQMNSLRAEDTAVYYCAAGSTSTATPLRVD | |
| H5 | DNTFYSNSVKGRFTISRDNSKNTVYLQMNSLRAEDTAVYYCAAGSTSTATPLRVD | |
| H6 | DNTFYSNSVKGRFTISRDNSKNTVYLQMNSLRAEDTAVYYCAAGSTSTATPLRVD | |
| H7 | DNTFYSNSVKGRFTISRDNSKNTLYLQMNSLRAEDTAVYYCAAGSTSTATPLRVD | |
| FC5 | YWGKGTQVTVSS | SEQ ID NO:1 |
| H1 | YWGQGTLVTVSS | SEQ ID NO:2 |
| H2 | YWGQGTLVTVSS | SEQ ID NO:3 |
| H3 | YWGQGTLVTVSS | SEQ ID NO:4 |
| H4 | YWGQGTLVTVSS | SEQ ID NO:5 |
| H5 | YWGQGTLVTVSS | SEQ ID NO:6 |
| H6 | YWGQGTLVTVSS | SEQ ID NO:7 |
| H7 | YWGQGTLVTVSS | SEQ ID NO:8 |

FIG. 1

HUMANIZED ANTIBODIES TRANSMIGRATING THE BLOOD-BRAIN BARRIER AND USES THEREOF

CROSS-REFERENCE TO RELATED APPLICATIONS

This application is a national stage filing under 35 U.S.C. § 371 of International Patent Application Serial No. PCT/IB2017/054036 filed on Jul. 4, 2017, which claims benefit from U.S. Provisional Patent Application No. 62/358,777 filed on Jul. 6, 2016, the contents of which are herein incorporated by reference.

FIELD OF THE INVENTION

The present invention relates to humanized antibodies and fragments thereof that transmigrate the blood-brain barrier, and uses thereof. More specifically, the present invention relates to antibodies and fragments thereof derived by humanization of an existing antibody. The antibodies of the present invention show enhanced binding to the brain endothelial antigen and improved transmigration across the blood-brain barrier.

BACKGROUND OF THE INVENTION

Neurodegenerative diseases, such as Alzheimer's and Parkinson's disease, are an increasing burden on our ageing society as there are currently no effective treatments for these disabling conditions. Treatment as well as early diagnosis of these and other diseases that originate in the brain remain challenging because the majority of suitable therapeutic molecules and diagnostics cannot penetrate the tight and highly restrictive blood-brain barrier (BBB) (Abbott, 2013). The BBB constitutes a physical barricade that is formed by brain endothelial cells (BEC) that line the blood vessels and connect with each other through tight junctions (Abbott, 2013). The tight junctions formed between the BEC are essential for the integrity of the BBB and prevent the paracellular transport of hydrophilic molecules larger than 500 daltons (Da). Because brain endothelial cells exhibit very low pinocytosis rates (Abbott, 2013), transcellular transport of larger molecules is limited to the highly specific receptor mediated transcytosis (RMT) pathway, and the passive, charge-based adsorption mediated transcytosis (Abbott, 2013; Pardridge, 2002). Additionally, the high density of efflux pumps, such as P-glycoprotein or the multi-drug resistance protein-1 (MDR-1), contribute to the removal of unwanted substances from the brain (Abbott, 2013).

While all these characteristics protect the brain from pathogens and toxins, they equally prevent the entry of most therapeutics. In fact, less than 5% of small molecule therapeutics and virtually none of the larger therapeutics can cross the BBB in pharmacologically relevant concentrations (i.e., sufficient to engage a central nervous system (CNS) target and elicit pharmacologic/therapeutic response) unless they are specifically 'ferried', that is, coupled to a transporter molecule. Due to the lack of effective 'carriers' to transport molecules across the BBB, numerous drugs against neurodegenerative diseases have been 'shelved' or eliminated from further development as they cannot be delivered to the brain in sufficient amount.

Different approaches to deliver larger molecules into the brain have been explored. For example, the integrity of the BBB may be disrupted, resulting in a leaky BBB, which in turn allows for unrestricted, paracellular entry of larger molecules into the brain. Tight junctions can be successfully loosened or disrupted by various approaches. For example, injection of substances that induce osmotic shock (for example, mannitol, hypertonic solutions) into the blood stream causes cell shrinkage and results in the disruption of tight junctions, therefore severely compromising the BBB (Guillaume, 2010). Other modulators of tight junctions include alkylglycerols, bradykinin and several analogues thereof, as well as viruses that modulate expression of proteins involved in maintaining the tight junctions (Erdlenbruch et al., 2003; Preston et al., 2008; Gan et al., 2013). A more localized disruption of the BBB is possible through application of ultrasound (Nhan et al., 2013). However, the periods during which the BBB is disrupted are sufficient to alter brain homeostasis and allow harmful chemicals, toxins and pathogens to enter the brain; this can result in serious side-effects, e.g., seizures and brain swelling, infection and possibly permanent neuropathological changes. Therefore, repeated treatments with these techniques for chronic and diffuse brain diseases affecting multiple brain regions are not practical. Most of these treatments are costly, necessitate hospitalisation, and some approaches require anesthesia.

Another approach for circumventing the BBB is direct injection of therapeutic molecules into the cerebrospinal fluid (CSF), the parenchymal space, or other parts of the brain. Several delivery methods have been developed, including: intracerebral (intra-parenchymal), intraventricular, and intrathecal delivery via infusion or convection-enhanced diffusion (CED) pumps. However, any type of direct injection into the brain or intracerebral implant is an invasive and costly procedure, as it requires hospitalization, anesthesia, and often surgery. Moreover, the poor diffusion rates of the therapeutics, particularly large biologics, within brain parenchyma limit the penetration of therapeutics to only small areas surrounding the site of injection/implantation. The correct placement of injections, catheters, and implants is challenging yet crucial to achieve diffusion of the drug to the targeted region of the brain. Additionally, catheters and implants provide a site for infection and/or immune response against the foreign material.

In another attempt to increase delivery across the BBB, CNS drugs have been modified to increase their brain uptake. Such modifications can include a change of their surface charge, a reduction in molecule size, and change to the lipohilicity of the drugs. However, any modifications to increase brain penetration are also likely to alter the overall pharmacology of the drug, including its desired activity and/or specificity. In addition, lipophilic molecules are more prone to being exported from the brain through the P-glycoprotein efflux pump.

Finally, endogenous transport mechanisms across the BBB have been exploited. Physiological mechanisms that allow transport of large molecules across the BBB can be divided into the highly specific receptor mediated transcytosis (RMT) and the non-specific charge based adsorptive mediated endocytosis pathways. Endocytosis is triggered upon binding of the specific ligand to its receptor, or upon electrostatic interaction between the cationic ligand or drug and the anionic functional groups on the brain endothelial cell surface (luminal side), respectively. Subsequently, the newly formed endosome is transcytosed across the cell to the abluminal side, to release its cargo.

Because adsorptive mediated transcytosis is non-specific, charge-mediated interaction, it occurs in all vascular beds and organs, limiting the availability of drug for brain delivery. Therefore, exploiting the RMT pathway remains the only physiological, non-invasive yet highly receptor-specific brain delivery method.

Only a few receptors are presently known to undergo RMT at the BBB and 'ferry' across their natural ligands: the well-studied transferrin receptor (TfR), the insulin receptor (IR), low-density lipoprotein receptor related proteins 1 and 2 (LRP-1 and -2) and diphtheria toxin receptor Peptides, natural ligands, and antibodies or antibody fragments have been developed that bind to these receptors (Pardridge et al., 1991; Yu et al., 2011; Muruganandam et al., 2001; Abulrob et al., 2005; Demeule, 2008; Sumbria et al., 2013), functioning as drug-to-brain transporters that utilize endogenous RMT pathways. Recently, antibodies against CD98hc, a component of the large neutral amino acid transporter (LAT1), have been shown to undergo transcytosis across the BBB (Zuchero et al., 2016), suggesting that this transporter could be another target for developing BBB carriers. However, to date only a single peptide (Angiopep ANG1005, targeting LRP-1) has been analyzed in phase II clinical studies, while other candidates are being studied in laboratory settings or are just entering Phase 1 studies. The RMT pathway appears to be the most promising pathway for transport of biologic drugs into the brain, but current approaches have limitations, including non-selective expression of the target receptor at the BBB, competition between the carrier and the natural ligands to the receptor, ineffective transcytosis of a receptor, as well as lysosomal degradation of endocytosed carriers (Xiao and Gun, 2013).

The lack of high-capacity and high-selectivity BBB carriers that do not disrupt the physiology and homeostasis of the BBB delays the development of new therapeutics and diagnostics for diseases originating in the brain, including brain tumors and neurodegenerative diseases.

SUMMARY OF THE INVENTION

The present invention relates antibodies and fragments thereof that transmigrate the blood-brain barrier, and uses thereof. More specifically, the present invention relates to antibodies and fragments thereof derived by humanization of an existing antibody. The antibodies of the present invention show enhanced binding to the brain endothelial antigen and improved transmigration across the blood-brain barrier.

The present invention provides an isolated or purified antibody or fragment thereof, comprising the sequence (SEQ ID NO: 9)

$X_1$VQLVESGGGLVQPGGSLRLSCAASGFKITHYTMGW$X_2$RQAPGK$X_3$$X_4$E$X_5$

VSRITWGGDNTFYSNSVKGRFTISRDNSKNT$X_6$YLQMNSLRAEDTAVYYC

AAGSTSTATPLRVDYWGQGTLVTVSS, where $X_1$ = D or E, $X_2$ = F or V, $X_3$ = E or G, $X_4$ = R or L, $X_5$ = F or W, $X_6$ = L or V.

For example, the isolated or purified antibody or fragment thereof of the present invention may be selected from any one of

EVQLVESGGGLVQPGGSLRLSCAASGFKITHYTMGWVRQAPGKGLEWVSR

ITWGGDNTFYSNSVKGRFTISRDNSKNTLYLQMNSLRAEDTAVYYCAAGS

-continued

TSTATPLRVDYWGQGTLVTVSS (SEQ ID NO: 2, referred to herein as FC5-H1);

EVQLVESGGGLVQPGGSLRLSCAASGFKITHYTMGWVRQAPGKGLEWVSR

ITWGGDNTFYSNSVKGRFTISRDNSKNTVYLQMNSLRAEDTAVYYCAAGS

TSTATPLRVDYWGQGTLVTVSS (SEQ ID NO: 3, also referred to herein as FC5-H2);

EVQLVESGGGLVQPGGSLRLSCAASGFKITHYTMGWFRQAPGKGLEFVSR

ITWGGDNTFYSNSVKGRFTISRDNSKNTVYLQMNSLRAEDTAVYYCAAGS

TSTATPLRVDYWGQGTLVTVSS (SEQ ID NO: 4, also referred to herein as FC5-H3);

DVQLVESGGGLVQPGGSLRLSCAASGFKITHYTMGWFRQAPGKGLEFVSR

ITWGGDNTFYSNSVKGRFTISRDNSKNTVYLQMNSLRAEDTAVYYCAAGS

TSTATPLRVDYWGQGTLVTVSS (SEQ ID NO: 5, also referred to herein as FC5-H4);

DVQLVESGGGLVQPGGSLRLSCAASGFKITHYTMGWFRQAPGKGREFVSR

ITWGGDNTFYSNSVKGRFTISRDNSKNTVYLQMNSLRAEDTAVYYCAAGS

TSTATPLRVDYWGQGTLVTVSS (SEQ ID NO: 6, also referred to herein as FC5-H5);

DVQLVESGGGLVQPGGSLRLSCAASGFKITHYTMGWFRQAPGKEREFVSR

ITWGGDNTFYSNSVKGRFTISRDNSKNTVYLQMNSLRAEDTAVYYCAAGS

TSTATPLRVDYWGQGTLVTVSS (SEQ ID NO: 7, also referred to herein as FC5-H6);
and

EVQLVESGGGLVQPGGSLRLSCAASGFKITHYTMGWFRQAPGKEREFVSR

ITWGGDNTFYSNSVKGRFTISRDNSKNTLYLQMNSLRAEDTAVYYCAAGS

TSTATPLRVDYWGQGTLVTVSS (SEQ ID NO: 8, also referred to herein as FC5-H7).

In the invention as described herein, the isolated or purified antibody or fragment thereof may be in a multivalent display format, using any suitable multimerizing technology. For example, the isolated or purified antibody or fragment thereof may be linked to a Fc fragment, thus forming a dimer. In this embodiment the Fc fragment may be any suitable Fc fragment, for example the Fc from mouse IgG2b or from human IgG1. In a specific example, the Fc may comprise the sequence of SEQ ID NO:20.

The isolated or purified antibody or fragment thereof of the present invention may transmigrate the blood-brain barrier.

The present invention also encompasses a nucleic acid molecule encoding the isolated or purified antibody or fragment thereof as described herein. Vectors comprising the nucleic acid molecule encoding the isolated or purified antibody or fragment thereof are also included in the scope of the present invention.

The isolated or purified antibody or fragment thereof of the present invention may be immobilized onto a surface.

In another application, the isolated or purified antibody or fragment thereof as described above may be linked to a cargo molecule. Any suitable cargo molecule may be used.

The cargo molecule may have a molecular weight in the range of about 1 kDa to about 200 kDa. For example, and without wishing to be limiting, the cargo molecule may be a detectable agent, a therapeutic, a drug, a peptide, a growth factor, a cytokine, a receptor trap, a chemical compound, a carbohydrate moiety, an enzyme, an antibody or fragment thereof, a DNA-based molecule, a viral vector, or a cytotoxic agent; one or more liposomes or nanocarriers loaded with a detectable agent, a therapeutic, a drug, a peptide, an enzyme, an antibody or fragment thereof, a DNA-based molecule, a viral vector, or a cytotoxic agent; or one or more nanoparticle, nanowire, nanotube, or quantum dots. In such a construct, the isolated or purified antibody or fragment thereof carries the cargo molecule across the blood-brain barrier.

The present invention further encompasses a composition comprising one or more than one isolated or purified antibody or fragment thereof as described above and a pharmaceutically-acceptable carrier, diluent, or excipient.

Presently, humanized variants of blood-brain barrier-crossing antibody FC5 are presented. Humanization of the antibody aims to reduce potential immunogenicity in humans due to amino acid residues of camelid origin within the $V_HH$. Not only were the CDR sequences of the FC5 antibody grafted onto a human heavy-chain framework, but back-mutations (to selected amino-acid residues of the parental camelid sequence) were also introduced into the fully-humanized framework sequence. Surprisingly, it was generally found that humanized variants showed improved thermal stability as reflected by the melting temperature (Tm) values compared to parental camelid FC5, with one variant (FC5-H3) showing an exceptional Tm-increase of more than 10° C. compared to the parental FC5. Furthermore, most humanized FC5 constructs showed improved affinity for SV-ARBEC-expressed receptor, with one variant (FC5-H7) showing an unexpectedly significant increase compared to the parental FC5. Importantly, this trend is further consistent the binding improvements against human brain endothelial cells (HBEC)-D3 afforded by humanized variants versus the parental camelid FC5. Finally, the humanized variants exhibit in vitro cell permeability capabilities that are at least at the level of the parental FC5 antibody, and increased to as much as 165% for some of the humanized variants.

BRIEF DESCRIPTION OF THE DRAWINGS

These and other features of the invention will now be described by way of example, with reference to the appended drawings, wherein:

FIG. 1 is an alignment of sequences of FC5 $V_HH$ and its humanized variants.

FIG. 4 shows the $P_{app}$ values in in vitro BBB model of the FC5 and its humanized variants (H1-H7). Equimolar amounts (1.25 μM) of each variant of FC5 and a negative control (A20.1, a *Clostridium difficile* toxin A-binding $V_HH$) were tested simultaneously for their ability to cross a rat in vitro BBB model.

FIG. 5 shows binding and transmigration of Fc fusions of FC5 and FC5-H7 in vitro.

DETAILED DESCRIPTION OF THE INVENTION

Figure 2:
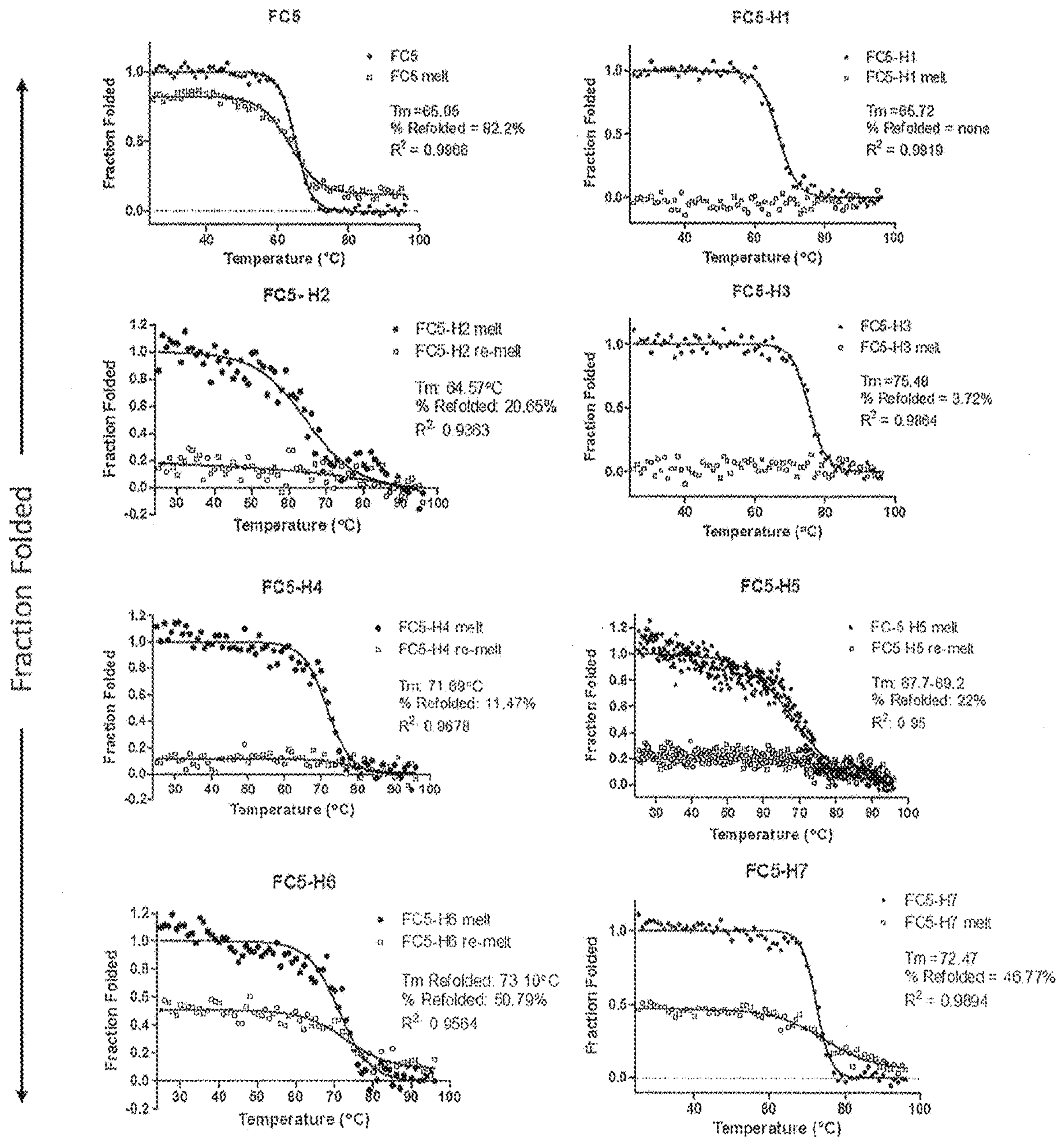
FIG. 2 shows the melting temperature (Tm) as determined by circular dichroism (CD) for FC5 $V_HH$ and its humanized variants (labelled FC5-H1, FC5-H2, FC5-H3, FC5-H5, FC5-H6, FC5-H7). The proteins were heated to above 90° C. and measurements were taken in the CD instrument to determine the melting curve (black or filled circles) and the Tm. Subsequently, the proteins were cooled to room temperature, heated once more and analysed by CD (grey curve or squares). This allowed the determination of the fraction of refolded protein.

The present invention relates antibodies and fragments thereof that transmigrate the blood-brain barrier, and uses thereof. More specifically, the present invention relates to antibodies and fragments thereof derived by humanization of an existing antibody. The antibodies of the present invention show enhanced binding to the brain endothelial antigen and improved transmigration across the blood-brain barrier.

The present invention provides an isolated or purified antibody or fragment thereof, comprising the sequence (SEQ ID NO: 9)
$X_1$VQLVESGGGLVQPGGSLRLSCAASGFKITHYTMGW$X_2$RQAPGK$X_3X_4$E$X_5$VSRITWGGDNTFYSNSVKGRFTISRDNSKNT$X_6$YLQMNSLRAEDTAVYYCAAGSTSTATPLRVDYWGQGTLVTVSS, where $X_1$ = D or E, $X_2$ = F or V, $X_3$ = E or G, $X_4$ = R or L, $X_5$ = F or W, $X_6$ = L or V.

The term "antibody", also referred to in the art as "immunoglobulin" (Ig), as used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen-binding determinants of the molecule, and thus determines the specificity of an antibody for its target antigen. The majority of sequence variability occurs in six hypervariable regions, three each per variable heavy ($V_H$) and light ($V_L$) chain; the hypervariable regions combine to form the antigen-binding site, and contribute to binding and recognition of an antigenic determinant. The specificity and affinity of an antibody for its antigen is determined by the structure of the hypervariable regions, as well as their size, shape, and chemistry of the surface they present to the antigen. Various schemes exist for identification of the regions of hypervariability, the two most common being those of Kabat and of Chothia and Lesk. Kabat et al (1991) define the "complementarity-determining regions" (CDR) based on sequence variability at the antigen-binding regions of the $V_H$ and $V_L$ domains. Chothia and Lesk (1987) define the "hypervariable loops" (H or L) based on the location of the structural loop regions in the $V_H$ and $V_L$ domains. These individual schemes define CDR and hypervariable loop regions that are adjacent or overlapping, those of skill in the antibody art often utilize the terms "CDR" and "hypervariable loop" interchangeably, and they may be so used herein. The CDR/loops are identified herein according to the Kabat scheme.

An "antibody fragment" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may include, but is not limited to a Fv, single-chain Fv (scFv; a molecule consisting of $V_L$ and $V_H$ connected with a peptide linker), Fab, F(ab')$_2$, single-domain antibody (sdAb; a fragment composed of a single $V_L$ or $V_H$), and multivalent presentations of any of these. Antibody fragments such as those just described may require linker sequences, disulfide bonds, or other type of covalent bond to link different portions of the fragments; those of skill in the art will be familiar with the requirements of the different types of fragments and various approaches for their construction.

In a non-limiting example, the antibody fragment may be an sdAb derived from naturally-occurring sources. Heavy chain antibodies of camelid origin (Hamers-Casterman et al, 1993) lack light chains and thus their antigen binding sites consist of one domain, termed $V_H$H. sdAb have also been observed in shark and are termed $V_{NAR}$ (Nuttall et al, 2003). Other sdAb may be engineered based on human Ig heavy and light chain sequences (Jespers et al, 2004; To et al, 2005). As used herein, the term "sdAb" includes those sdAb directly isolated from $V_H$, $V_H$H, $V_L$, or $V_{NAR}$ reservoir of any origin through phage display or other technologies, sdAb derived from the aforementioned sdAb, recombinantly produced sdAb, as well as those sdAb generated through further modification of such sdAb by humanization, affinity maturation, stabilization, solubilization, camelization, or other methods of antibody engineering. Also encompassed by the present invention are homologues, derivatives, or fragments that retain the antigen-binding function and specificity of the sdAb.

SdAb possess desirable properties for antibody molecules, such as high thermostability, high detergent resistance, relatively high resistance to proteases (Dumoulin et al, 2002) and high production yield (Arbabi-Ghahroudi et al, 1997); they can also be engineered to have very high affinity by isolation from an immune library (Li et al, 2009) or by in vitro affinity maturation (Davies & Riechmann, 1996). Further modifications to increase stability, such as the introduction of non-canonical disulfide bonds (Hussack et al, 2011; Kim et al, 2012), may also be brought to the sdAb.

A person of skill in the art would be well-acquainted with the structure of a single-domain antibody (see, for example, 3DWT, 2P42 in Protein Data Bank). An sdAb comprises a single immunoglobulin domain that retains the immunoglobulin fold; most notably, only three CDR/hypervariable loops form the antigen-binding site. However, and as would be understood by those of skill in the art, not all CDR may be required for binding the antigen. For example, and without wishing to be limiting, one, two, or three of the CDR may contribute to binding and recognition of the antigen by the sdAb of the present invention. The CDR of the sdAb or variable domain are referred to herein as CDR1, CDR2, and CDR3.

The present invention encompasses an antibody fragment that is "humanized". Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In the process of CDR grafting, one or more than one of the CDR defined herein may be fused or grafted to a human variable region ($V_H$, or $V_L$), to other human antibody (IgA, IgD, IgE, IgG, and IgM), to antibody fragment framework regions (Fv, scFv, Fab), or to proteins of similar size and nature onto which CDR can be grafted (Nicaise et al, 2004). In such a case, the conformation of said one or more than one hypervariable loop is likely preserved, and the affinity and specificity of the sdAb for its target (i.e., brain endothelial cells) is likely minimally affected. CDR grafting is known in the art (for example, see Tsurushita et al, 2005; Jones et al, 1986; Tempest et al, 1991; Riechmann et al, 1988; Queen et al, 1989; reviewed in Gonzales et al, 2005—see also references cited therein), and thus persons of skill would be amply familiar with methods of preparing such humanized antibody fragments and humanizing amino acid positions.

The antibody or fragment thereof of the present invention is a humanized version of the FC5 antibody described in WO 2002/057445. FC5 (SEQ ID NO:1) binds to the surface of brain endothelial cells and subsequently transmigrates the blood-brain barrier (BBB). FC5 has also been shown to act as a carrier to usher molecules of various sizes across the BBB (see for example, WO 2011/127580). The antigen mediating FC5 transmigration was identified as transmembrane domain protein 30A (TMEM30A; WO 2007/036021), which is enriched on the surface of brain endothelial cells.

For example, and without wishing to be limiting in any manner, the isolated or purified antibody or fragment thereof as described above may be selected from the group consisting of:

```
EVQLVESGGGLVQPGGSLRLSCAASGFKITHYTMGWVRQAPGKGLEWVSR
ITWGGDNTFYSNSVKGRFTISRDNSKNTLYLQMNSLRAEDTAVYYCAAGS
TSTATPLRVDYWGQGTLVTVSS (SEQ ID NO: 2, referred to
herein as FC5-H1);
EVQLVESGGGLVQPGGSLRLSCAASGFKITHYTMGWVRQAPGKGLEWVSR
ITWGGDNTFYSNSVKGRFTISRDNSKNTVYLQMNSLRAEDTAVYYCAAGS
TSTATPLRVDYWGQGTLVTVSS (SEQ ID NO: 3, also
referred to herein as FC5-H2);
EVQLVESGGGLVQPGGSLRLSCAASGFKITHYTMGWFRQAPGKGLEFVSR
ITWGGDNTFYSNSVKGRFTISRDNSKNTVYLQMNSLRAEDTAVYYCAAGS
TSTATPLRVDYWGQGTLVTVSS (SEQ ID NO: 4, also
referred to herein as FC5-H3);
DVQLVESGGGLVQPGGSLRLSCAASGFKITHYTMGWFRQAPGKGLEFVSR
ITWGGDNTFYSNSVKGRFTISRDNSKNTVYLQMNSLRAEDTAVYYCAAGS
TSTATPLRVDYWGQGTLVTVSS (SEQ ID NO: 5, also
referred to herein as FC5-H4);
DVQLVESGGGLVQPGGSLRLSCAASGFKITHYTMGWFRQAPGKGREFVSR
ITWGGDNTFYSNSVKGRFTISRDNSKNTVYLQMNSLRAEDTAVYYCAAGS
TSTATPLRVDYWGQGTLVTVSS (SEQ ID NO: 6, also
referred to herein as FC5-H5);
DVQLVESGGGLVQPGGSLRLSCAASGFKITHYTMGWFRQAPGKEREFVSR
ITWGGDNTFYSNSVKGRFTISRDNSKNTVYLQMNSLRAEDTAVYYCAAGS
TSTATPLRVDYWGQGTLVTVSS (SEQ ID NO: 7, also
referred to herein as FC5-H6);
EVQLVESGGGLVQPGGSLRLSCAASGFKITHYTMGWFRQAPGKEREFVSR
ITWGGDNTFYSNSVKGRFTISRDNSKNTLYLQMNSLRAEDTAVYYCAAGS
TSTATPLRVDYWGQGTLVTVSS (SEQ ID NO: 8, also
referred to herein as FC5-H7);
and
a sequence subsantially identical thereto.
```

A substantially identical sequence may comprise one or more conservative amino acid mutations. It is known in the art that one or more conservative amino acid mutations to a reference sequence may yield a mutant peptide with no substantial change in physiological, chemical, physico-chemical or functional properties compared to the reference sequence; in such a case, the reference and mutant sequences would be considered "substantially identical" polypeptides. A conservative amino acid substitution is defined herein as the substitution of an amino acid residue for another amino acid residue with similar chemical properties (e.g. size, charge, or polarity). These conservative amino acid mutations are made to the framework regions of the sdAb while maintaining the CDR sequences of FC5 (residues 26-35, 50-66, 99-111 of SEQ ID NO:1 to 9) and the overall structure of the CDR of the antibody or fragment; thus the specificity and binding of the antibody are maintained. Furthermore, framework residues contributing to the humanization of the sdAb should also be maintained (residues 1, 5, 14, 37, 44, 45, 47, 75, 79, 87, 88, 93, 114, and 117 of SEQ ID NO:2-9).

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pKa value of greater than 7, which are typically positively charged at physiological pH. Basic amino acids include arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms, for example histidine (His or H). Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences of the present invention may be at least 90% identical; in another example, the substantially identical sequences may be at least 90, 91, 92, 93, 94, 95, 96, 97, 98, 99, or 100% identical, or any percentage therebetween, at the amino acid level to sequences described herein. Importantly, the substantially identical sequences retain the activity and specificity of the reference sequence. In a non-limiting embodiment, the difference in sequence identity may be due to conservative amino acid mutation(s). In a non-limiting example, the present invention may be directed to an antibody or fragment thereof comprising a sequence at least 95%, 98%, or 99% identical to that of the antibodies described herein.

The antibody or fragment thereof of the present invention may also comprise additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence (for example, but not limited to ompA), a detection/purification tag (for example, but not limited to c-Myc, $His_5$, or $His_6$), or a combination thereof. In another example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags, or may serve as a detection/purification tag.

The antibody or fragment thereof of the present invention may also be in a multivalent display format, also referred to herein as multivalent presentation. Multimerization may be achieved by any suitable method of known in the art. For example, and without wishing to be limiting in any manner, multimerization may be achieved using self-assembly molecules such as those described in WO2003/046560, where pentabodies are produced by expressing a fusion protein comprising the antibody or fragment thereof of the present invention and the pentamerization domain of the B-subunit of an $AB_5$ toxin family (Merritt & Hol, 1995). A multimer may also be formed using the multimerization domains described by Zhu et al. (2010); this form, referred to herein as a "combody" form, is a fusion of the antibody or fragment of the present invention with a coiled-coil peptide resulting in a multimeric molecule. Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection (Nielson et al, 2000), c-jun/Fos interaction (de Kruif & Logtenberg, 1996), "Knob into holes" interaction (Ridgway et al, 1996), or using the azymetric platform (Von Kreudenstein et al, 2014).

Another method known in the art for multimerization is to dimerize the antibody or fragment thereof using an Fc domain, for example, but not limited to mouse or human Fc domains. Human Fc domains may be selected from various classes including, but not limited to, IgG, IgM, or various subclasses including, but not limited to IgG1, IgG2, etc. In this approach, the Fc gene in inserted into a vector along with the sdAb gene to generate a sdAb-Fc fusion protein (Bell et al, 2010; lqbal et al, 2010); the fusion protein is recombinantly expressed then purified. For example, and without wishing to be limiting in any manner, multivalent display formats may encompass chimeric formats of FC5-H7 and its mutational variants linked to an Fc domain. Such antibodies are easy to engineer and to produce, can greatly extend the serum half-life of sdAb, and may be excellent tumor imaging reagents (Bell et al., 2010).

The Fc domain in the multimeric complex as just described may be any suitable Fc fragment known in the art. The Fc fragment may be from any suitable source; for example, the Fc may be of mouse or human origin. In a specific, non-limiting example, the Fc may be from the mouse IgG2b isotype or from human IgG1 isotype (Bell et al, 2010; lqbal et al, 2010). In a specific, non-limiting example, the multimerized isolated or purified antibody or fragment as just described may comprise an Fc comprising the sequence of SEQ ID NO:20.

Each subunit of the multimers described above may comprise the same or different antibodies or fragments thereof of the present invention, which may have the same or different specificity. Additionally, the multimerization domains may be linked to the antibody or antibody fragment using a linker, as required; such a linker should be of sufficient length and appropriate composition to provide flexible attachment of the two molecules, but should not hamper the antigen-binding properties of the antibody.

The antibody or fragment thereof as described herein may transmigrate across the blood-brain barrier. The brain is separated from the rest of the body by a specialized endothelial tissue known as the blood-brain barrier (BBB). The endothelial cells of the BBB are connected by tight junctions and efficiently prevent many therapeutic compounds from entering the brain. In addition to low rates of vesicular transport, one specific feature of the BBB is the existence of enzymatic barrier(s) and high level(s) of expression of ATP-dependent transporters on the abluminal (brain) side of the BBB, including P-glycoprotein (Gottesman et al., 1993; Watanabe, 1995), which actively transport various molecules from the brain into the blood stream (Samuels, 1993). Only small (<500 Daltons) and hydrophobic (Pardridge, 1995) molecules can more readily cross the BBB. Thus, the ability of the antibody or fragment thereof as described above to specifically bind the surface receptor, internalize into brain endothelial cells, and undergo transcytosis across the BBB by evading lysosomal degradation is useful in the neurological field.

The present invention also encompasses nucleic acid sequences encoding the molecules as described herein. Given the degeneracy of the genetic code, a number of nucleotide sequences would have the effect of encoding the polypeptide, as would be readily understood by a skilled artisan. The nucleic acid sequence may be codon-optimized for expression in various micro-organisms. The present invention also encompasses vectors comprising the nucleic acids as just described. Furthermore, the invention encompasses cells comprising the nucleic acid and/or vector as described.

The present invention further encompasses the isolated or purified antibody or fragments thereof immobilized onto a surface using various methodologies; for example, and without wishing to be limiting, the antibody or fragment may be linked or coupled to the surface via His-tag coupling, biotin binding, covalent binding, adsorption, and the like. Immobilization of the antibody or fragment thereof of the present invention may be useful in various applications for capturing, purifying or isolating proteins. The solid surface may be any suitable surface, for example, but not limited to the well surface of a microtiter plate, channels of surface plasmon resonance (SPR) sensorchips, membranes, beads (such as magnetic-based or sepharose-based beads or other chromatography resin), glass, plastic, stainless steel, a film, or any other useful surface such as nanoparticles, nanowires and cantilever surfaces.

The invention also encompasses the antibody or fragment thereof as described above linked to a cargo molecule. The cargo molecule may be any suitable molecule, which is delivered across the BBB by the antibody or fragment thereof. The cargo molecule may have a molecular weight in the range of about 1 kDa to about 200 kDa; for example, the cargo molecule may have a molecular weight of about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kDa, or any weight therebetween, or any range of weights defined by any two aforementioned weights. In specific, non-limiting examples, the cargo molecule may have a molecular weight of 1 kDa (for example, but not limited to a small molecule such as Cy5.5), 1-10 kDa (for example, but not limited to a peptide such as galanin, 3 kDa), about 80 kDa (for example, but not limited to a Fc fragment, enzyme, protein, antibody etc), or about 180 kDa (for example, but not limited to a monoclonal antibody).

For example, and without wishing to be limiting in any manner, the cargo molecule may be a detectable agent, a therapeutic agent, a drug, a peptide, an enzyme, a growth factor, a cytokine, a receptor trap, an antibody or fragment thereof (e.g., IgG, scFv, Fab, $V_HH$, etc) a chemical compound, a carbohydrate moiety, DNA-based molecules (anti-sense oligonucleotide, microRNA, siRNA, plasmid), a cytotoxic agent, viral vector (adeno-, lenti-, retro), one or more liposomes loaded with any of the previously recited types of cargo molecules, or one or more nanoparticle, nanowire, nanotube, or quantum dots. The cargo molecule as described above may be a detectable agent. For example, the FC5 antibody variant or fragment thereof may be linked to a radioisotope, a paramagnetic label, a fluorophore, a fluorescent agent, Near Infra-Red (NIR; for example Cy5.5) fluorochrome or dye, an echogenic microbubble, an affinity label, a detectable protein-based molecule, nucleotide, quantum dot, nanoparticle, nanowire, or nanotube or any other suitable agent that may be detected by imaging methods. The antibody or fragment thereof may be linked to the cargo molecule using any method known in the art (recombinant technology, chemical conjugation, etc.).

The cargo molecule as described herein may be linked, also referred to herein as "conjugated", to the antibody or fragment thereof by any suitable method known in the art. For example, and without wishing to be limiting, the cargo molecule may be linked to the peptide by a covalent bond or ionic interaction. The linkage may be achieved through a chemical cross-linking reaction, or through fusion using recombinant DNA methodology combined with any peptide expression system, such as bacteria, yeast or mammalian cell-based systems. When conjugating the cargo molecule to the antibody or fragment thereof, a suitable linker may be used. Methods for linking an antibody or fragment thereof to a cargo molecule such as a therapeutic or detectable agent would be well-known to a person of skill in the art.

In one non-limiting example, the cargo molecule may be a detectable label, a radioisotope, a paramagnetic label such as gadolinium or iron oxide, a fluorophore, Near Infra-Red (NIR) fluorochrome or dye, an echogenic microbubble, an affinity label (for example biotin, avidin, etc), enzymes, or any other suitable agent that may be detected by diagnostic imaging methods. In a specific, non-limiting example, the anti-IGF1R-5 or fragment thereof may be linked to a near infrared fluorescence (NIRF) imaging dye, for example and not wishing to be limiting Cy5.5, Alexa680, Dylight680, or Dylight800.

The in vivo detection step in the methods described above may be whole body imaging for diagnostic purposes or local imaging at specific sites, such as but not limited to brain vessels or brain tumor vessels, in a quantitative manner to assess the progression of disease or host response to a treatment regimen. The detection step in the methods as described above may be immunohistochemistry, or a non-invasive (molecular) diagnostic imaging technology including, but not limited to:

- Optical imaging;
- Positron emission tomography (PET), wherein the detectable agent is an isotopes such as $^{11}C$, $^{13}N$, $^{15}O$, $^{18}F$, $^{64}Cu$, $^{62}Cu$, $1^{24}I$, $^{76}Br$, $^{82}Rb$ and $^{6}8Ga$, with $^{18}F$ being the most clinically utilized;
- Single photon emission computed tomography (SPECT), wherein the detectable agent is a radiotracer such as $^{99m}Tc$, $^{111}In$, $^{123}I$, $^{201}Tl$, $^{133}Xe$, depending on the specific application;
- Magnetic resonance imaging (MRI), wherein the detectable agent may be, for example and not limited to gadolinium, iron oxide nanoparticles and carbon-coated iron-cobalt nanoparticles thereby increasing the sensitivity of MRI for the detection of plaques;
- Contrast-Enhanced Ultrasonography (CEUS) or ultrasound, wherein the detectable agent is at least one acoustically active and gas-filled microbubble. Ultrasound is a widespread technology for the screening and early detection of human diseases. It is less expensive than MRI or scintigraphy and safer than molecular imaging modalities such as radionuclide imaging because it does not involve radiation.

The present invention further provides a method of transporting a molecule of interest across the blood-brain barrier. The method comprises administering the molecule linked to an antibody or fragment thereof as described herein to a subject. The molecule may be any desired molecule, including the cargo molecules, as previously described; the molecule may be "linked" to the antibody or fragment thereof using any suitable method, including, but not limited to conjugation or expression in a fusion protein. The administration may be by any suitable method, for example parenteral administration, including but not limited to intravenous (iv), subcutaneous (sc), and intramuscular (im) administration. In this method, the antibody or fragment thereof of the present invention 'ferries' the molecule of interest across the BBB to its brain target.

The present invention also encompasses a composition comprising one or more than one isolated or purified antibody or fragment thereof as described herein. The composition may comprise a single antibody or fragment as described above, or may be a mixture of antibodies or fragments. Furthermore, in a composition comprising a mixture of antibodies or fragments of the present invention, the antibodies may have the same specificity, or may differ in their specificities;

The composition may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form, powder form (for example, but limited to lyophilised or encapsulated), capsule or tablet form. For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the antibody or fragment thereof. Dry powders may also include additives to improve stability and/or carriers to increase bulk/volume; for example, and without wishing to be limiting, the dry powder composition may comprise sucrose or trehalose. In a specific, non-limiting example, the composition may be so formulated as to deliver the antibody or fragment thereof to the gastrointestinal tract of the subject. Thus, the composition may comprise encapsulation, time-release, or other suitable technologies for delivery of the antibody or fragment thereof. It would be within the competency of a person of skill in the art to prepare suitable compositions comprising the present compounds.

The present invention will be further illustrated in the following examples. However, it is to be understood that these examples are for illustrative purposes only and should not be used to limit the scope of the present invention in any manner.

Example 1: Humanization of FC5

To avoid potential immunogenicity in humans, llama-derived FC5 (SEQ ID NO:1) was humanized by mutation of "camelid" residues in the $V_HH$. It should be noted that, for the purpose of humanization, Kabat numbering (Kabat et al, 1991) was used for identification of CDR residues.

3D-structure modeling of camelid $V_HHs$. Template structures similar to FC5 $V_HH$ were identified using BLAST searches against the Protein Data Bank (PDB). The 3D structure of the FC5 $V_HH$ was approximated using homology modeling based on the 2X1O|A (PDB code|Chain ID) structure as template. The FC5 $V_HH$ structure was then built by mutating the template structure to the FC5 sequence; this included 32 mutations at various positions (26 in the CDR and 6 in the framework region). The FC5 $V_HH$ model was then refined by energy minimization with the AMBER force-field and a stepwise release of constraints, ranging from the CDR loops, which were relaxed first, to the backbone heavy atoms of the framework region, which were fully relaxed only in the last stage. The CDR-H3 loop of the $V_HH$ model was then refined by Monte-Carlo-minimization (MCM) conformational sampling, in which dihedral angles in the CDR-H3 region were sampled followed by energy minimization.

Selection of the human heavy-chain framework for the camelid CDR. Human heavy-chain framework was selected by standard sequence homology comparison against the human germline databases (VBASE), against other sequence databases (Genbank and SwissProt), and against the human framework consensus sequences. BLAST searches were conducted to retrieve sequence matches with highest homology in the framework region only (i.e., excluding CDR) while matching the length of the CDR. The closest human frameworks identified for FC5 $V_HH$ corresponded to the human VH-3 subgroup. Several human germline VH-3 framework sequences that were most similar to FC5 $V_HH$ were also retained in addition to the human VH-3 consensus sequence. The FC5 $V_HH$ framework sequences required 16 mutations in order to arrive at the consensus human VH-3 sequence for 100% framework humanization.

Identification of framework residues for back-mutations. The FC5 $V_HH$ model and its fully-humanized counterpart were characterized to estimate the humanness index, antigen contact propensity index, to delineate the CDR, canonical residues, unusual framework residues, potential glycosylation sites, buried residues, Vernier zone residues, and proximity to CDR. The analysis of these data suggested the design of several humanized variants for the anti-IGF1R $V_HH$, each variant having varying numbers of back-mutations to the parent camelid residues at various positions. A total of 7 humanized variants were designed for FC5 $V_HH$ (FC5-H1, FC5-H2, FC5-H3, FC5-H4, FC5-H5, FC5-H6, FC5-H7), where variants contained up to 7 back-mutations (FIG. 1). Some of these camelid back-mutations residues were buried inside the $V_HH$ domain core and hence were not expected to induce a B-cell mediated immune response.

Example 2: Cloning, Expression and Purification of FC5 and its Humanized Variants FC5 single domain antibody (sdAb) or its humanized variants as described in Example 1 (FC5-H1, FC5-H2, FC5-H3, FC5-H4, FC5-H5, FC5-H6, FC5-H7) were cloned, transformed, expressed and purified in preparation for testing in vitro. All variants were expressed in fusion with His5 and c-myc tags) to allow for purification by immobilized metal affinity chromatography using HiTrap Chelating™ column and for detection by immunochemistry, respectively.

Briefly, DNA encoding sdAb FC5 (SEQ ID NO:1) or humanized variants was cloned into the Bbsl/BamHl sites of plasmid pSJF2H to generate expression vector for FC5 (Muruganandam et al, 2001). The DNA constructs were confirmed by nucleotide sequencing on 373A DNA Sequencer Stretch (PE Applied Biosystems) using primers fdTGIII, 5'-GTGAAAAAATTATTATTATTCGCAATTCCT-3' (SEQ ID NO:10) and 96GIII, 5'-CCCTCATAGTTAGCGTAACG-3' (SEQ ID NO:11).

The constructs were transformed into *E. coli* strain TG1 and single colonies were used to inoculate 100 ml of M9 medium containing 100 μg/ml of ampicillin, and the culture was shaken overnight at 200 rpm at 37° C. The grown cells (25 ml) were transferred into 1 L of M9 medium (0.2% glucose, 0.6% $Na_2HPO_4$, 0.3% $KH_2PO_4$, 0.1% $NH_4Cl$, 0.05% NaCl, 1 mM $MgCl_2$, 0.1 mM $CaCl_2$) supplemented with 5 μg/ml of vitamin B1, 0.4% casamino acid, and 100 μg/ml of ampicillin. The cell culture was shaken at room temperature for 24 hours at 200 rpm and subsequently supplemented with 100 ml of 10× induction medium Terrific Broth containing 12% Tryptone, 24% yeast extract, and 4% glycerol. Protein expression was induced by adding isopropyl-p-D-thiogalactopyranoside (IPTG; 1 mM). After induction, the culture was shaken for an additional 72 hours at 25° C., and the periplasmic fraction was extracted by the osmotic shock method.

The FC5 and its humanized variants were purified by immobilized metal-affinity chromatography using HiTrap Chelating™ column (Amersham Pharmacia Biotech; Piscataway, N.J.). Bound FC5 or variant was eluted in 10 mM HEPES buffer, 500 mM NaCl, pH 7.0, with a 10-500 mM imidazole gradient and peak fractions were extensively dialyzed against 10 mM HEPES buffer, 150 mM NaCl, 3.4 mM EDTA, pH 7.4. Protein concentration was also determined.

Example 3: Biophysical Characterization of Humanized FC5 Variants

The FC5 $V_HH$ and humanized variants prepared in Example 2 were characterized using melting temperature analyses.

Melting temperature: The thermal stability of the FC5 $V_HH$ and humanized variants was evaluated using melting temperature ($T_m$) measurement by CD spectroscopy. A Jasco J-815 spectropolarimeter equipped with a Peltier thermoelectric type temperature control system (Jasco, Easton, Md., USA) was used to carry out experiments. A CD cuvette with a path length of 1 mm was used. The spectra were recorded over a wavelength range of 180-260 nm with scanning speed of 50 nm/min, digital integration time (DIT) of 4 s, a bandwidth of 1 nm, data pitch of 1 nm, and an integration time of 1 s. To measure melting temperature or $T_m$ Greenfield, 2006), CD spectra were recorded over a temperature range of 30° C. to 96° C. All CD spectra were subtracted from the blank corresponding to buffer spectra. Measurements were performed with 50 µg/mL $V_H$H in 100 mM sodium phosphate buffer, pH 7.4. Heat-induced protein denaturation was monitored at 210 nm for all variants. The fraction folded (ff) was obtained by a formula as described (Greenfield, 2006a; 2006b):

$$ff=([\theta]_T-[\theta]_U)/([\theta]_F-[\theta]_U) \qquad \text{formula I}$$

where $[\theta]_T$ is the molar ellipticity at any temperature, $[\theta]_F$, is the molar ellipticity of the fully folded protein at 30° C. and $[\theta]_U$ is the molar ellipticity of the unfolded protein at 90° C. Melting temperature ($T_m$) was obtained as a midpoint of the unfolding curve (fraction folded, ff, versus temperature) by a nonlinear regression curve fit (Boltzmann sigmoidal equation) using the graphing software GraphPad Prism (version 4.02 for Windows). The melting temperatures ($T_m$) of $V_H$H were determined based on ellipticity data assuming a two-state system, which is in agreement with the observed denaturation curves corresponding to a sharp transition into denaturation The $T_m$ values were taken at midpoint of the sigmoidal denaturation curves of fraction folded (ff) versus temperature.

Results are shown in FIG. 2. Humanized variants FC5-H1, FC5-H3, FC5-H4, FC5-H5, FC5-H6, and FC5-H7 showed improved Tm values (>65° C.) compared to parental camelid FC5 (<65° C.)—a surprising result, as it was not a targeted goal in the design of the variants. Among humanized variants, FC5-H7 showed the best re-folding capacity, while FC5-H3 showed an 11° C. increase in Tm compared to FC5.

Example 4: Binding of FC5 Mutational Variants to Brain Endothelial Cells

To evaluate the effect of humanization on binding of the antibodies to their cellular antigens, binding of FC5 and its humanized variants to SV-ARBEC cells or human microvascular brain endothelial cells (HBEC-D3) was measured.

Mirrorball 6 High Sensitivity Microplate Cytometry (TTP Labtech): All buffers and reagents were pre-chilled to 4° C. Each $V_H$H single domain antibody was diluted to a starting concentration of 1000 nM in a 1:1 buffer mix of 0.5×PBS/2.5 mM EDTA and Mirrorball assay buffer—Live Cell Imaging Solution, LCIB (Invitrogen, 140 mM NaCl, 2.5 mM KCl, 1.8 mM $CaCl_2$, 1.0 mM $MgCl_2$, 20 mM Hepes, pH 7.4, mOsm=300). A 20 µl volume of a 1:1 mix of LCIB and 0.5×PBS/2.5 mM EDTA was added to all wells of each 384 well Mirrorball assay plate (Corning 3712); with the exception of row A which received 40 µl of 1000 nM test $V_H$H antibody. Serial dilutions were prepared for each test variant within the Mirrorball 384 well assay plate. A 16-channel Finn pipette (Thermo Scientific) was used to transfer 20 µl of $V_H$H antibody from row A-columns 1-24 into row B-columns 1-24 mixing 8×, then transferring 20 µl of $V_H$H antibody from row B-columns 1-24 into row C-columns 1-24 mixing 8×. Dilutions were repeated until row G-columns 1-24 to create 7 point curve for each $V_H$H antibody variant. A second set of test $V_H$H antibody variants (1000 nM) were added to row I-columns 1-24 and the dilution protocol was repeated until row 0-columns 1-24. Row H-columns 1-24 were reserved on each plate for the reference FC5-H7 $V_H$H single domain antibody. Row P-columns 1-24 received no antibody; this was background control for non-specific binding of the secondary to the cells of interest; thus 48 variants could be tested on each 384 well Mirrorball assay plate. Immortalized adult rat brain microvascular endothelial cells (SV-ARBEC) and/or human microvascular brain endothelial cells (HBEC-D3) were dissociated in Accutase solution (Sigma Aldrich) to generate single cell populations. Cells were washed in LCIB then centrifuged at 200×g, 5 min to pellet. Wash buffer was removed and the cell pellet was re-suspended into 1 mL of LCIB. Cell number was calculated using a Bio-Rad TC20 automated cell counter with Trypan Blue dye to assess viability. The cells were diluted to 350,000 live cells/ml using LCIB. A fluorescent conjugate c-myc Alexa 488 detection antibody (1600 ng/ml, Santa Cruz Biotechnology) supplemented with Draq 5 nuclear stain (2 uM, Cell Signaling) was prepared in LCIB assay buffer. The cells and the detection secondary/Drag 5 solution were mixed 1:1 and 20 µl of solution containing 3500 cells was added into each well of the Mirrorball 384 well assay plate; which already contained each $V_H$H antibody variant in a 7 point dilution series resulting in a final concentration of 500, 250, 125, 62.5, 31.25, 15.63 and 7.81 nM. All plates were incubated at 4° C. for 2 h and 20 h. Readings were taken at each time point using Mirrorball High Sensitivity Microplate Cytometry with the following settings:

- Laser Settings: 488 and 640 enabled, 6.0 mW;
- Channel Settings: FL-2 (488-540 nm) voltage 600, sensitivity 4, Tiff files saved and FL-4 (650-690 nm) voltage 600, sensitivity 4, trigger 4, Tiff files saved;
- Object Characteristics: FL-2 (peak intensity, mean intensity, total intensity, and baseline) and FL-4 (peak intensity, mean intensity, total intensity and baseline);
- Population Definition: Objects—Cells Filters (FL-4 perimeter range 0-500 nm and FL-2 mean intensity range 0-15000);
- Population Statistics: Objects: number of objects, Objects: mean (FL-2 peak, mean, total intensities and perimeter) and Objects: mean FL-2 baseline. Objects: median (FL-2 peak, mean, and total intensities) Objects: mean (FL-4 peak, mean, total intensities and perimeter) and Objects: mean FL-4 baseline. Objects: median (FL-4 peak, mean, and total intensities) Cells: number of objects, Cells: mean (FL-2 peak, mean, and total intensities) and Cells: mean FL-2 baseline. Cells: median (FL-2 peak, mean, and total intensities) Cells: mean (FL-4 peak, mean, and total intensities) and Cells: mean FL-4 baseline. Cells: median (FL-4 peak, mean, and total intensities).

The remaining live cell material was incubated at 4° C. adjacent to the assay plate to monitor cell viability at 2 h and 20 h time points. The Mirrorball assay procedure was repeated for FC5 and all humanized variants in both SV-ARBEC and HBEC-D3 cell lines of interest. The data was analysed with Cellista software (TTP Labtech) and GraphPad Prism 6 software programs.

Figure 3:
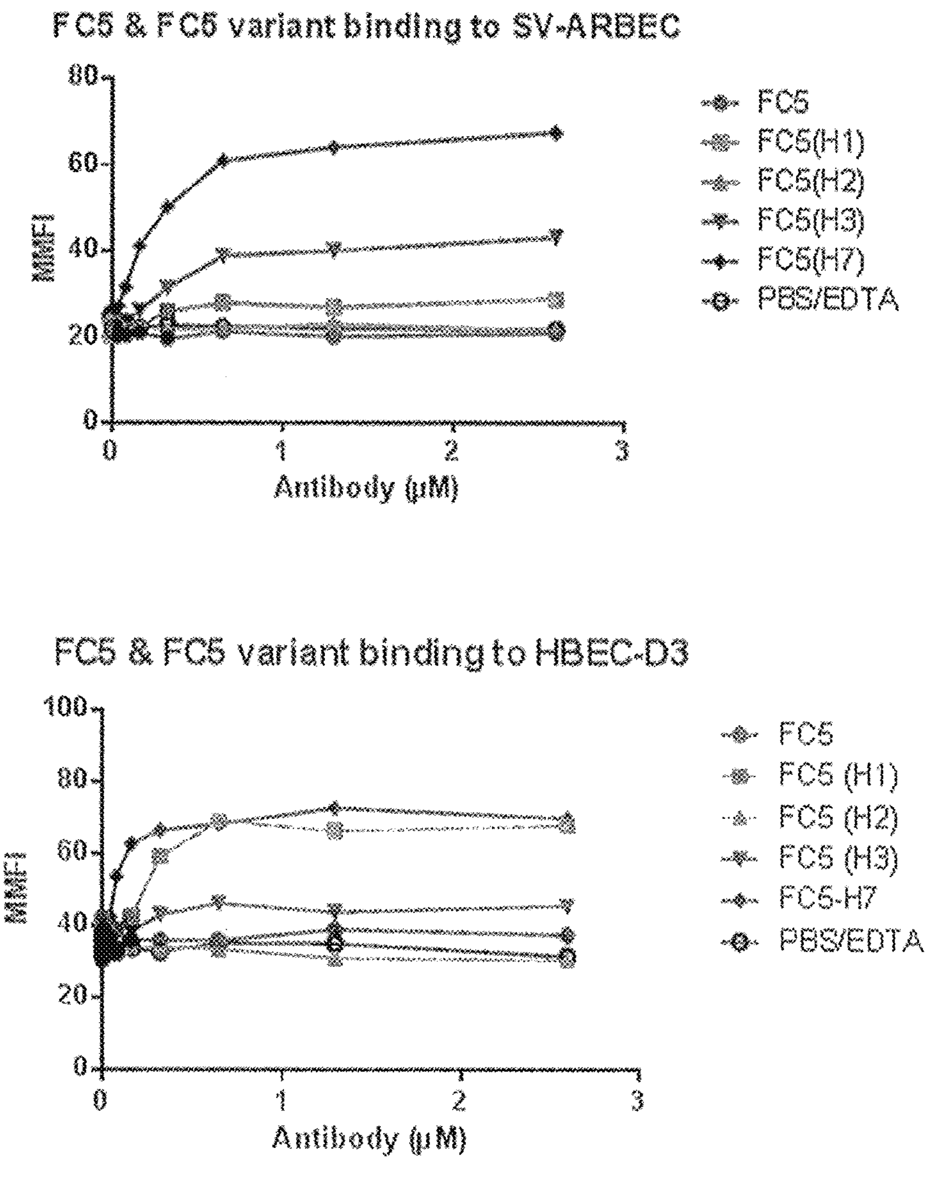
FIG. 3 shows binding curves of FC5 $V_HH$ and its humanized variants to rat brain endothelial cells (SV-ARBEC) or human microvascular brain endothelial cells (HBEC-D3) in suspension determined using Mirrorball instrument. Serial dilutions were prepared for each test variant within the Mirrorball 384 well assay plate to create a 7-point binding curve. A fluorescent conjugate c-myc Alexa 488 detection antibody (1600 ng/ml, Santa Cruz Biotechnology) supplemented with Draq 5 nuclear stain (2 uM, Cell Signaling) was used for detection of cell-bound antibody. All plates were incubated at 4° C. for 4 h. Readings were taken using Mirrorball High Sensitivity Microplate Cytometry as described below.

Results of FC5 and humanized variants binding to SV-ARBEC cells and to HBEC-D3 cells are shown in FIG. 3 (some results not shown). Compared to very weak binding of FC5 to SV-ARBEC or to HBEC-D3 cells in this assay, humanized FC5 variants FC5-H1, FC5-H3, FC5-H4, FC5-H5, FC5-H6 and FC5-H7 all show improved binding to SV-ARBEC cells; humanized variants FC5-H3, FC5-H2 and FC5-H7 also show improved binding to HBEC-D3. Notably FC5-H7 shows highly improved binding to the SV-ARBEC cells and also to the HBEC-D3 cells, indicating a significantly improved affinity of this variant to its receptor(s) on these cells.

Example 5: Transport of the FC5 and FC5 Humanized Variants Across In Vitro Blood Brain Barrier Model To evaluate whether humanized FC5 variants of Example 2 transmigrate the blood-brain barrier, an in vitro assay was used as described below.

SV40-immortalized Adult Rat Brain Endothelial Cells (SV-ARBEC) were used to generate an in vitro blood-brain barrier (BBB) model as described (Garberg et al., 2005; Haqqani et al., 2012). SV-ARBEC (80,000 cells/membrane) were seeded on a 0.1 mg/mL rat tail collagen type I-coated tissue culture inserts (pore size 1 μm; surface area 0.9 $cm^2$, Falcon) in 1 ml of growth medium. The bottom chamber of the insert assembly contained 2 ml of growth medium supplemented with the immortalized neonatal rat astrocytes-conditioned medium in a 1:1 (v/v) ratio.

Equimolar amounts (5.6 μM) of positive (FC5) or negative controls (A20.1, a *Clostridium difficile* toxin A binding $V_HH$;), and humanized variants of Example 2 were tested for their ability to cross this rat in vitro BBB model. Following exposure of equimolar amounts of the sdAb to the luminal side of the BBB, samples were taken after 15, 30 and 60 min from the abluminal side. The sdAb content of each sample was then quantified by mass spectrometry (multiple reaction monitoring-isotype labeled internal standards; MRM-ILIS), see below.

MRM-ILIS: The methods are all as described in Haqqani et al. (2012). Briefly, to develop the SRM (selected reaction monitoring also known as multiple reaction monitoring, MRM) assay for $V_HH$, each $V_HH$ was first analyzed by nanoLC-MS/MS using data-dependent acquisition to identify all ionizible peptides. For each peptide, the 3 to 5 most intense fragment ions were chosen. An initial SRM assay was developed to monitor these fragments at attomole amounts of the digest (about 100-300 amol). Fragments that showed reproducible intensity ratios at low amounts (i.e., had Pearson $r^2 \geq 0.95$ compared to higher amounts) were considered stable and were chosen for the final SRM assay. To further optimize the assay, elution times for each peptide were also included, with care taken to not choose peptides that have close m/z (mass-to-charge ratio) and elution times.

A typical multiplexed SRM analysis of $V_HH$ in cell media involved spiking known amount of ILIS (0.1-10 nM) followed by injecting 100-400 ng of cultured media proteins (0.3-1 μL) into the nanoLC-MS system. The precursor m/z of each target peptide ion was selected in the ion trap (and the remaining unrelated ions were discarded) at the specified elution time for the target, followed by collision induced dissociation (CID) fragmentation, and selection of only the desired fragment ions in the ion trap for monitoring by the detector. For quantification analysis, raw files generated by the LTQ (ThermoFisher) were converted to the standard mass spectrometry data format mzXML and intensities were extracted using an in-house software called Q-MRM (Quantitative-MRM; see Haqqani et al. 2012), which is a modified version of MatchRx software. For each $V_HH$, extracted-ion chromatograms were generated for each of its fragment ion that consisted of combined intensities within 0.25 Da of the fragment m/z over the entire elution time. To obtain a final intensity value for each fragment, all intensities within 0.5 min of the expected retention times were summed. A $V_HH$ was defined as detectable in a sample if the fragments of at least one of its peptides showed the expected intensity ratios, i.e., the final intensity values showed a strong Pearson correlation $r^2 \geq 0.95$ and $p<0.05$ compared with the final intensities values of its corresponding pure $V_HH$.

Media samples containing mixtures of $V_HH$ were reduced, alkylated and trypsin-digested as previously described (Haqqani et al., 2012; Gergov et al., 2003). The digests (tryptic peptides) were acidified with acetic acid (5% final concentration) and analyzed on a reversed-phase nanoAcquity UPLC (Waters, Milford, Mass.) coupled to LTQ XL ETD or LTQ Orbitrap ETD mass spectrometer (ThermoFisher, Waltham, Mass.). The desired aliquot of the sample was injected and loaded onto a 300 μm I.D.×0.5 mm 3 μm PepMaps C18 trap (ThermoFisher) then eluted onto a 100 μm I.D.×10 cm 1.7 μm BEH130C18 nanoLC column (Waters) using a gradient from 0%-20% acetonitrile (in 0.1% formic) in 1 min, 20%-46% in 16 min, and 46%-95% in 1 min at a flow rate of 400 nL/min. The eluted peptides were ionized into the mass spectrometer by electrospray ionization (ESI) for MS/MS and SRM analysis using CID for fragmentation of the peptide ions. The CID was performed with helium as collision gas at normalized collision energy of 35% and 30 ms of activation time. Ion injection times into linear ion trap were adjusted by the instrument using an automatic gain control (AGC) target value of $6\times10^3$ and a maximum accumulation time of 200 ms The specific peptides used for detection and quantification of FC5 and its humanized variants, and control $V_HH$ A20.1 in multiplexed assay are shown in Table 1.

TABLE 1

Peptides used in nanoLC-SRM detection of FC5, FC5-ILIS, A20.1 and FC5 humanized variants. In various studies described, assays were multiplexed in different combinations for simultaneous monitoring in the same sample; (a) Heavy-labeled peptide; Limits of detection and quantification of the SRM assay for each peptide ranged from 1.5-2.5 ng/ml. 1 ng/mL corresponds to about 60-70 pM of $V_HH$. A20.1 as described in Hussack et al, 2011b).

| Protein | Signatures | SEQ ID NO: | Unique |
|---|---|---|---|
| FC5 | ITWGGDNTFYSNSVK | 12 | Yes |
| FC5-ILIS | ITWGGDNTFYSNSVK[(a)] | 12 | Yes |

TABLE 1-continued

Peptides used in nanoLC-SRM detection of FC5, FC5-ILIS, A20.1 and FC5 humanized variants. In various studies described, assays were multiplexed in different combinations for simultaneous monitoring in the same sample; (a) Heavy-labeled peptide; Limits of detection and quantification of the SRM assay for each peptide ranged from 1.5-2.5 ng/ml. 1 ng/mL corresponds to about 60-70 pM of $V_H$H. A20.1 as described in Hussack et al, 2011b).

| Protein | Signatures | SEQ ID NO: | Unique |
|---|---|---|---|
| A20.1 | TTYYADSVK | 13 | Yes |
| | EFVAAGSSTGR | 14 | Yes |
| | TFSMDPMAWFR | 15 | Yes |
| | DEYAYWGQGTQVTVSSGQAGQGSEQK | 16 | Yes |
| H1, H7 | LSCAASGFK | 17 | Yes |
| | NTLYLQMNSLR | 18 | Yes |
| | ITWGGDNTFYSNSVK | 12 | Yes |
| H2, H3, H4, H5, H6 | LSCAASGFK | 19 | Yes |
| | ITWGGDNTFYSNSVK | 12 | Yes |

Figure 4A:
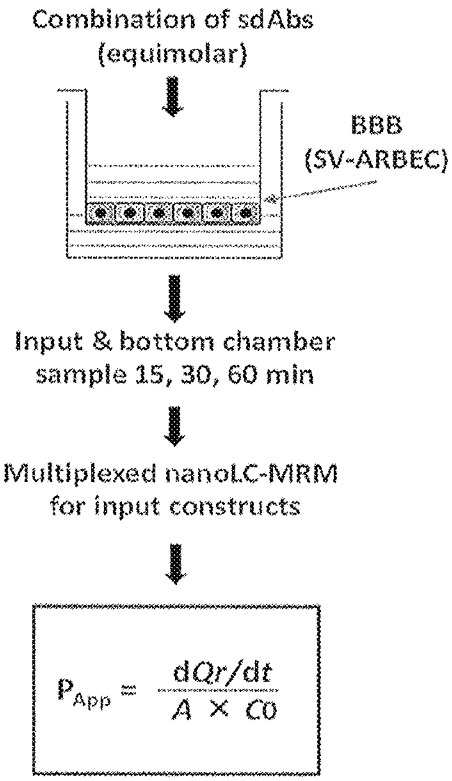
FIG. 4A shows Transwell in vitro BBB model. SV40-immortalized brain endothelial cells from adult rat (svARBECs) are grown in a monolayer on the membrane of an insert in the presence of rat astrocyte-conditioned medium in the bottom chamber and standard medium in the top chamber. Following co-addition of equimolar amounts of the various $V_HH$ to the luminal side of the BBB model, samples were taken from the bottom chamber after 15, 30 and 60 min. The concentrations of each $V_HH$ were then quantified in these samples by mass spectrometry (multiple reaction monitoring-isotype labeled internal standards; MRM-ILIS). The $P_{app}$ value, calculated using given formula [Qr/dt=cumulative amount in the receiver compartment versus time; A=area of the cell monolayer; C0=initial concentration of the dosing solution], is used to determine the ability of a molecule to cross the BBB. The results are average $P_{app}$ values obtained in 5-6 Transwell experiments.

Determination of the apparent permeability coefficient: Quantified values can be directly plotted or the $P_{app}$ (apparent permeability coefficient) values can be determined using formula given in FIG. 4A [Qr/dt=cumulative amount in the receiver compartment versus time; A=area of the cell monolayer; C0=initial concentration of the dosing solution] and plotted. The $P_{app}$ value is commonly used to determine the ability of a molecule to cross the BBB. $P_{app}$ values are a measure of the specific permeability of the compound across brain endothelial monolayer.

Figure 4B:
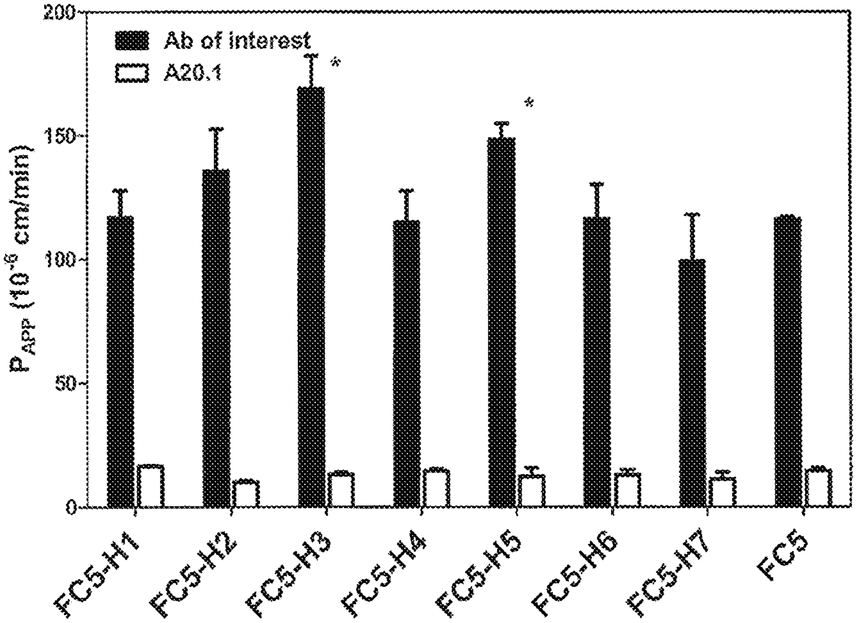
FIG. 4B shows $P_{app}$ values for FC5 and its humanized variants H1-H7. All variants showed enhanced BBB crossing compared to negative control A20.1 $V_HH$. FC5-H3 and FC5-H5 showed statistically ($p<0.05$; Student's t-test) higher $P_{app}$ values compared to the parent FC5.

Results are shown in FIGS. 4B&C. The results given are average $P_{app}$ values obtained from several independent experiments. Negative control A20.1 antibody has a very low $P_{app}$ value, indicating that non-specific transport or paracellular transport of this $V_H$H across the BBB model is minimal. FC5 $V_H$H shows $P_{app}$ value of ~100×10$^{-6}$ cm/min, while $P_{app}$ value of its humanized variant FC5-H3 is higher by 45% and $P_{app}$ value of humanized variant FC5-H5 is higher by 28%.

A summary of the characteristics of each humanized variant is shown in Table 2. Variants FC5-H1, FC5-H3, FC5-H4, FC5-H5, FC5-H6 and FC5-H7 show higher melting temperatures compared to camelid FC5. Variants FC5-H1, FC5-H3 and FC5-H7 show improved binding to both rat and human brain endothelial cells compared to camelid FC5. Variants FC5-H3 and FC5-H5 show significantly improved in vitro blood-brain barrier crossing compared to camelid FC5.

TABLE 2

Summary of melting temperature (Tm), cell binding (SV-ARBEC and HBEC-D3), and in vitro BBB permeability ($P_{APP}$) values of humanized FC5 variants in comparison to the parental camelid FC5 antibody.

| FC5 variant | % framework humanization | # camelid residues in framework | Tm (° C.) | $P_{APP}$ ($10^{-6}$ cm/min) | SV-ARBEC binding | HBEC-D3 binding |
|---|---|---|---|---|---|---|
| FC5 camelid | N/A | N/A | 65.1 | 110 ± 11 | 20.3 | 39.1 |
| FC5-H1 | 98.8 | 1 | 65.7 | 117 ± 18 | 27.0 | 66.4 |
| FC5-H2 | 97.6 | 2 | 64.6 | 135 ± 29 | 23.1 | 31.0 |
| FC5-H3 | 95.1 | 4 | 75.5 | 182 ± 3* | 40.2 | 43.9 |
| FC5-H4 | 93.9 | 5 | 71.7 | 115 ± 22 | n.d | n.d |
| FC5-H5 | 92.6 | 6 | 68.5 | 148 ± 9* | n.d | n.d |
| FC5-H6 | 91.5 | 7 | 71.3 | 116 ± 24 | n.d | n.d |
| FC5-H7 | 95.1 | 4 | 72.5 | 99 ± 26 | 64.2 | 72.8 |

SV-ARBEC and HBEC-D3 binding are expressed in MMFI units at an antibody concentration of 1.3 μM.
n.d.—not determined

Example 6: Expression and Purification of Humanized FC5-Fc Constructs

Constructs comprising FC5 or FC5-H7 fused to the N-terminus of human antibody Fc fragment of IgG1 were prepared, expressed, and purified.

The FC5 or FC5-H7 cDNA was cloned into mammalian expression vector pTT5 (Durocher 2002) containing the human Fc fragment. Polyplexes of the resulting vector were pre-formed by mixing 25 ml of plasmid DNA solution containing 187.5 μg pTT5-IR5mFc2b, 56.25 μg pTT-AK-Tdd (activated mutant of Protein Kinase B), 18.75 μg pTTo-GFP (to monitor transfection efficiency), and 112.5 μg of salmon testis DNA (Sigma-Aldrich); and 25 ml of PEI solution containing 1.125 mg of PEIpro™ (PolyPlus Transfection), both made in F17 medium. The mixture was incubated for 10 min prior to addition to the cell culture. A 450 ml culture of CHO cells stably expressing a truncated EBNA1 protein (CHO-3E7) and grown in F17 medium (Invitrogen) was transfected with 50 ml of polyplexes. Twenty four hours post-transfection, the culture was fed with 12.5 ml of 40% (w/v) tryptone N1 (Organotechnie) solution and 1.25 ml of 200 mM valproic acid solution. The culture was harvested 8 days post-transfection and clarified by centrifugation. Clarified medium was filtered through a 0.22 μm membrane prior to its application on a column packed with 5 ml of protein-A MabSelect SuRe resin (GE Healthcare). After loading, the column was washed with 5 volumes of phosphate-buffered saline pH 7.1 (PBS) and the antibody was eluted with 100 mM sodium citrate buffer pH 3.0. Fractions containing the eluted antibody were pooled and a buffer exchange was performed by loading on a desalting Econo-Pac column (BioRad) equilibrated in PBS. Desalted antibody was then sterile-filtered by passing through a Millex GP (Millipore) filter unit (0.22 μm) and aliquoted.

Example 7: Characterization of Humanized FC5-Fc Constructs

Figure 5A:
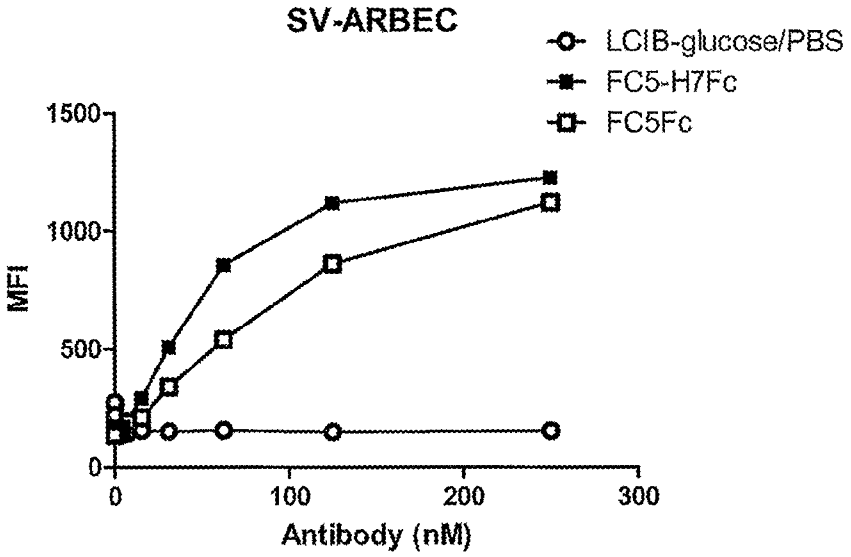
FIG. 5A shows binding of FC5Fc and FC5H7-Fc to rat brain endothelial cells (SV-ARBEC) in suspension determined using Mirrorball instrument. Serial dilutions were prepared for each test variant within the Mirrorball 384 well assay plate to create a 7-point binding curve. A fluorescent conjugate c-myc Alexa 488 detection antibody (1600 ng/ml, Santa Cruz Biotechnology) supplemented with Draq 5 nuclear stain (2 uM, Cell Signaling) was used for detection of cell-bound antibody. All plates were incubated at 4° C. for 4 h. Readings were taken using Mirrorball High Sensitivity Microplate Cytometry as described below.

The binding of Fc-fused FC5 and FC5-H7 (Example 6) to SV-ARBEC cells was evaluated using Mirrorball® High Sensitivity Microplate Cytometry (TTP Labtech) as described in Example 4. Results indicate that FC5-H7-Fc has slightly improved binding to SV-ARBEC compared to FC5-Fc (FIG. 5A).

Figure 5B:
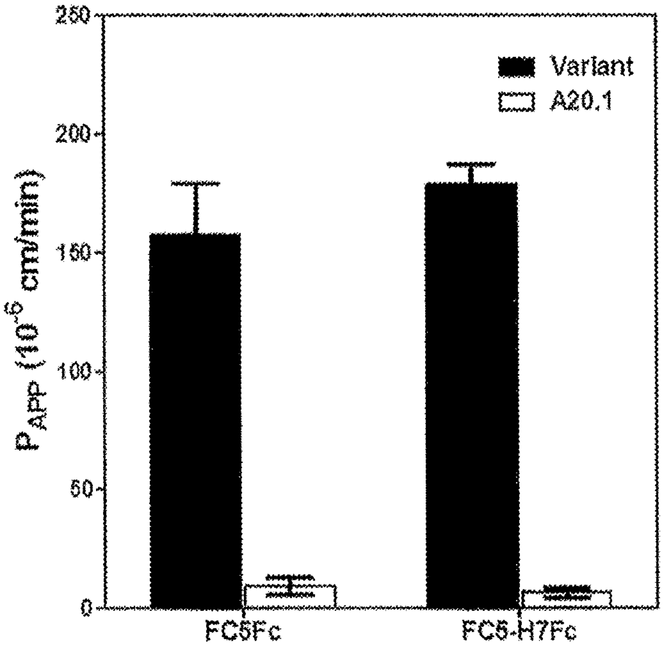
FIG. 5B shows Papp values of FCSFc and FC5H7-Fc in Transwell in vitro BBB model. The experiments were performed as described in FIG. 4.

To evaluate whether Fc-fused FC5-H7 from Example 6 transmigrate the blood-brain barrier, the in vitro assay and quantification method as described in Example 5 was used. The results indicate a similar $P_{app}$ for FC5-H7-Fc fusion compared to FC5-Fc (FIG. 5B), suggesting that the increased affinity of FC5H7 compared to FC5 did not affect its ability to transmigrate across the BBB in bi-valent format.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

LISTING OF SEQUENCES

| SEQ ID NO: | Sequences | Description |
|---|---|---|
| 1 | DVQLQASGGGLVQAGGSLRLSCAASGFKITHYTMGWFRQAPG KEREFVSRITWGGDNTFYSNSVKGRFTISRDNAKNTVYLQMNS LKPEDTADYYCAAGSTSTATPLRVDYWGKGTQVTVSS | FC5 |
| 2 | EVQLVESGGGLVQPGGSLRLSCAASGFKITHYTMGWVRQAPG KGLEWVSRITWGGDNTFYSNSVKGRFTISRDNSKNTLYLQMNS LRAEDTAVYYCAAGSTSTATPLRVDYWGQGTLVTVSS | FC5-H1 |
| 3 | EVQLVESGGGLVQPGGSLRLSCAASGFKITHYTMGWVRQAPG KGLEWVSRITWGGDNTFYSNSVKGRFTISRDNSKNTVYLQMNS LRAEDTAVYYCAAGSTSTATPLRVDYWGQGTLVTVSS | FC5-H2 |
| 4 | EVQLVESGGGLVQPGGSLRLSCAASGFKITHYTMGWFRQAPG KGLEFVSRITWGGDNTFYSNSVKGRFTISRDNSKNTVYLQMNS LRAEDTAVYYCAAGSTSTATPLRVDYWGQGTLVTVSS | FC5-H3 |
| 5 | DVQLVESGGGLVQPGGSLRLSCAASGFKITHYTMGWFRQAPG KGLEFVSRITWGGDNTFYSNSVKGRFTISRDNSKNTVYLQMNS LRAEDTAVYYCAAGSTSTATPLRVDYWGQGTLVTVSS | FC5-H4 |
| 6 | DVQLVESGGGLVQPGGSLRLSCAASGFKITHYTMGWFRQAPG KGREFVSRITWGGDNTFYSNSVKGRFTISRDNSKNTVYLQMNS LRAEDTAVYYCAAGSTSTATPLRVDYWGQGTLVTVSS | FC5-H5 |
| 7 | DVQLVESGGGLVQPGGSLRLSCAASGFKITHYTMGWFRQAPG KEREFVSRITWGGDNTFYSNSVKGRFTISRDNSKNTVYLQMNS LRAEDTAVYYCAAGSTSTATPLRVDYWGQGTLVTVSS | FC5-H6 |
| 8 | EVQLVESGGGLVQPGGSLRLSCAASGFKITHYTMGWFRQAPG KEREFVSRITWGGDNTFYSNSVKGRFTISRDNSKNTLYLQMNS LRAEDTAVYYCAAGSTSTATPLRVDYWGQGTLVTVSS | FCS-H7 |
| 9 | $X_1$VQLVESGGGLVQPGGSLRLSCAASGFKITHYTMGW$X_2$RQAP GK$X_3$$X_4$E$X_5$VSRITWGGDNIFYSNSVKGRFTISRDNSKNT$X_6$YLQ MNSLRAEDTAVYYCAAGSTSTATPLRVDYWGQGTLVTVSSV | Humanized FCS consensus sequence |
| 10 | GTGAAAAAATTATTATTATTCGCAATTCCT | fdTGIII primer |
| 11 | CCCTCATAGTTAGCGTAACG | 96GIII |
| 12 | ITWGGDNTFYSNSVK | Peptide for nano-LC-SRM |
| 13 | TTYYADSVK | Peptide for nano-LC-SRM |

-continued

LISTING OF SEQUENCES

| SEQ ID NO: | Sequences | Description |
|---|---|---|
| 14 | EFVAAGSSTGR | Peptide for nano-LC-SRM |
| 15 | TFSMDPMAWFR | Peptide for nano-LC-SRM |
| 16 | DEYAYWGQGTQVTVSSGQAGQGSEQK | Peptide for nano-LC-SRM |
| 17 | LSCAASGFK | Peptide for nano-LC-SRM |
| 18 | NTLYLQMNSLR | Peptide for nano-LC-SRM |
| 19 | LSCAASGFK | Peptide for nano-LC-SRM |
| 20 | AEPKSCDKTHTCPPCPAPELLGGPSVFLFPPKPKDTLMISRTPE VTCVVVDVSHEGPEVKFNWHVDGVEVHNAKTKPREEQYNSTY RVVSVLTVLHQDWLNGKEYKCKVSNKALPAPIEKTISKAKGQPR EPQVYTLPPSRDELTKNQVSLTCLVKGFYPSDIAVEWESNGQP ENNYKTTPPVLDSDGSFFLYSKLTVDKSRWQQGNVFSCSVMH EGLHNHYTQKSLSLSPG | IgG1 Fc |

REFERENCES

All patents, patent applications and publications referred to herein and throughout the application are hereby incorporated by reference.

Abbott N J (2013) Blood-brain barrier structure and function and the challenges for CNS drug delivery. J Inherit Metab Dis. 36(3):437-49.

Abulrob A, Sprong H, Van Bergen en Henegouwen P, Stanimirovic D (2005) The blood-brain barrier transmigrating single domain antibody: mechanisms of transport and antigenic epitopes in human brain endothelial cells. J Neurochem. 95(4):1201-14.

Arbabi-Ghahroudi, M. Desmyter A, Wyns L, Hamers R., and Muyldermans S (1997) Selection and identification of single domain antibody fragments from camel heavy-chain antibodies, FEBS Lett 414, 521-526

Bell A., Wang Z. J., Arbabi-Ghahroudi M., Chang T. A., Durocher Y., Trojahn U., Baardsnes J., Jaramillo M. L., Li S., Baral T. N., O'Connor-McCourt M., Mackenzie R., and Zhang J. (2010) Cancer Lett. 289, 81-90.

Chothia C., and Lesk A. M. (1987) J. Mol. Biol. 196, 901-917.

Davies J., and L. Riechmann, Affinity improvement of single antibody VH domains: residues in all three hypervariable regions affect antigen binding. Immunotechnology 2 (1996) 169-179

De Kruif, J., and Logtenberg, T. (1996) J. Biol. Chem. 271, 7630-7634.

Demeule M.; Currie J. C.; Bertrand Y.; Che C.; Nguyen T.; Regina A.; Gabathuler R.; Castaigne J. P.; Beliveau R. Involvement of the low-density lipoprotein receptor-related protein in the transcytosis of the brain delivery vector angiopep-2, J. Neurochem. 2008, 106, 1534-1544.

Dumoulin, M., Conrath, K., Van Meirhaighe, A., Meersman, F., Heremans, K., Frenken, L. G., Muyldermans, S., Wyns, L., and Matagne, A. (2002) Protein Sci 11, 500-515.

Eisenberg, D., Schwarz, E., Komaromy, M., and Wall, R. (1984) J. Mol. Biol. 179, 125-142

Erdlenbruch B, Alipour M, Fricker G, Miller D S, Kugler W, Eibl H, Lakomek M (2003) Alkylglycerol opening of the blood-brain barrier to small and large fluorescence markers in normal and C6 glioma-bearing rats and isolated rat brain capillaries. Br J Pharmacol. 140(7):1201-10.

Gan Y, Jing Z, Stetler R A, Cao G (2013) Gene delivery with viral vectors for cerebrovascular diseases. Front Biosci (Elite Ed). 5:188-203. Review.

Garberg, P.; Ball, M.; Borg, N.; Cecchelli, R.; Fenart, L.; Hurst, R. D.; Lindmark, T.; Mabondzo, A.; Nilsson, J. E.; Raub, T. J.; Stanimirovic, D.; Terasaki, T.; Oberg, J. O.; Osterberg, T. In vitro models for the blood-brain barrier, Toxicol. In Vitro 2005, 19, 299-334.

Gergov, M.; Ojanpera, I.; Vuori, E. Simultaneous screening for 238 drugs in blood by liquid chromatography-ion spray tandem mass spectrometry with multiple-reaction monitoring, J. Chromatogr. B Analyt. Technol. Biomed. Life Sci. 2003, 795, 41-53.

Gonzales N R, DePascalis R, Schlom J, Kashmiri S V S (2005) Tumor Biol 26, 31-43.

Gottesman et al., Ann. Rev. Biochem., 62, 385-427 (1993)

Greenfield N J (2006). Using circular dichroism collected as a function of temperature to determine the thermodynamics of protein unfolding and binding interactions. Nat Protoc. 1(6):2527-35.

Guillaume D J et al. Intra-arterial chemotherapy with osmotic blood-brain barrier disruption for aggressive oligodendroglial tumors: results of a phase I study. Neurosurgery, 66(1), 48-58 (2010);

Hamers-Casterman, C., Atarhouch, T., Muyldermans, S., Robinson, G., Hamers, C., Songa, E. B., Bendahman, N., and Hamers, R. (1993) Nature 363, 446-448.

Haqqani A S, Caram-Salas N, Ding W, Brunette E, Delaney C E, Baumann E, Boileau E, Stanimirovic D (2012) Multiplexed evaluation of serum and CSF pharmacokinetics of brain-targeting single-domain antibodies using a NanoLC-SRM-ILIS method. Mol Pharm. 2013 May 6; 10(5):1542-56.

Hussack G., Hirama T., Ding W., MacKenzie R., and Tanha J. (2011) PLoS ONE 6, e28218.

Hussack G, Arbabi-Ghahroudi M, van Faassen H, Songer J G, Ng K K, MacKenzie R, Tanha J (2011b) Neutralization of *Clostridium difficile* toxin A with single-domain antibodies targeting the cell receptor binding domain. J Biol Chem. 286(11): 8961-76.

Iqbal U., Trojahn U., Albaghdadi H., Zhang J., O'Connor M., Stanimirovic D., Tomanek B., Sutherland G., and Abulrob A. (2010) Br. J. Pharmacol. 160, 1016-1028.

Jespers, L., Schon, O., Famm, K., and Winter, G. (2004) Nat. Biotechnol. 22, 1161-1165.

Jones P T, Dear P H, Foote J, Neuberger M S, Winter G (1986) Nature 321, 522-525.

Kabat E A, Wu T T. Identical V region amino acid sequences and segments of sequences in antibodies of different specificities. Relative contributions of VH and VL genes, minigenes, and complementarity-determining regions to binding of antibody-combining sites. J Immunol. 1991; 147:1709-19.

Kim, D. Y., Kandalaft, H., Ding, W., Ryan, S., van Fassen, H., Hirama, T., Foote, S. J., MacKenzie, R., and Tanha, J. (2012) PEDS advance access Aug. 30, 2012, 1-9.

Li S, Zheng W, Kuolee R, Hirama T, Henry M, Makvandi-Nejad S, Fjallman T, Chen W, Zhang J. Pentabody-mediated antigen delivery induces antigen-specific mucosal immune response. Mol Immunol 2009; 46:1718-26.

Merritt, E. A., and Hol, W. G. (1995) Curr. Opin. Struct. Biol. 5, 165-171.

Muruganandam A, Tanha J, Narang S, Stanimirovic D (2001) Selection of phage-displayed llama single-domain antibodies that transmigrate across human blood-brain barrier endothelium. FASEB J. February; 16(2):240-2.

Nhan T, Burgess A, Cho E E, Stefanovic B, Lilge L, Hynynen K. (2013) Drug delivery to the brain by focused ultrasound induced blood-brain barrier disruption: Quantitative evaluation of enhanced permeability of cerebral vasculature using two-photon microscopy. J Control Release. 172(1):274-280.

Nicaise M, Valeio-Lepiniec M, Minard P, Desmadril M. (2004) Affinity transfer by CDR grafting on a nonimmunoglobulin scaffold. Protein Sci. 13(7): 1882-1891.

Nielsen, U. B., Adams, G. P., Weiner, L. M., and Marks, J. D. (2000) Cancer Res. 60, 6434-6440.

Nuttall, S. D., Krishnan, U. V., Doughty, L., Pearson, K., Ryan, M. T., Hoogenraad, N. J., Hattarki, M., Carmichael, J. A., Irving, R. A., and Hudson, P. J. (2003) Eur. J. Biochem. 270, 3543-3554.

Pardridge, W. M.; Buciak, J. L.; Friden, P. M. Selective transport of an anti-transferrin receptor antibody through the blood-brain barrier in vivo, J. Pharmacol. Exp. Ther. 1991, 259, 66-70.

Pardridge, W. M., Adv. Drug Delivery Reviews, 15, 5-36 (1995)

Pardridge, W. M. Drug and gene delivery to the brain: the vascular route, Neuron. 2002, 36, 555-558.

Preston E, Slinn J, Vinokourov I, Stanimirovic D. (2008) Graded reversible opening of the rat blood-brain barrier by intracarotid infusion of sodium caprate. J Neurosci Methods. 168(2):443-9.

Queen C, Schneider W P, Selick H E, Payne P W, Landolfi N F, Duncan J F, Avdalovic N M, Levitt M, Junghans R P, Waldmann T A (1989) Proc Natl Acad Sci USA 86, 10029-10033.

Ridgway, J. B., Presta, L. G., and Carter, P. (1996) Protein Eng. 9, 617-621.

Riechmann L, Clark M, Waldmann H, Winter G (1988) Nature 332, 323-327.

Samuels B. L., J. Clin. Pharmacol. Ther., 54, 421-429 (1993)

Sumbria R K, Zhou Q H, Hui E K, Lu J Z, Boado R J, Pardridge W M. (2013) Pharmacokinetics and brain uptake of an IgG-TNF decoy receptor fusion protein following intravenous, intraperitoneal, and subcutaneous administration in mice. Mol Pharm. 10(4):1425-31.

Tempest P R, Bremmer P, Lambert M, Taylor G, Furze J M, Carr F J, Harris W J (1991) Biotechnology 9, 266-271.

To, R., Hirama, T., Arbabi-Ghahroudi, M., MacKenzie, R., Wang, P., Xu, P., Ni, F., and Tanha, J. (2005) J. Biol. Chem. 280, 41395-41403.

Tsurushita N, Hinton, R P, Kumar S (2005) Design of humanized antibodies: From anti-Tac to Zenapax. Methods 36, 69-83.

von Kreudenstein T S, Lario P I, Dixit S B (2014) Protein engineering and the use of molecular modeling and simulation: the case of heterodimeric Fc engineering. Methods January 1; 65(1):77-94.

Watanabe, T., Acta Oncol., 34, 235-241 (1995)

Xiao G, Gan L S. (2013) Receptor-mediated endocytosis and brain delivery of therapeutic biologics. Int J Cell Biol. doi: 10.1155/2013/703545. Epub 2013 Jun. 11. Yaksh T L, Rudy T A (1976) Chronic catheterization of the spinal subarachnoid space. Physiol Behav. 17(6):1031-6.

Yu, Y. J.; Zhang, Y.; Kenrick, M.; Hoyte, K.; Luk, W.; Lu, Y.; Atwal, J.; Elliott, J. M.; Prabhu, S.; Watts, R. J.; Dennis, M. S. Boosting brain uptake of a therapeutic antibody by reducing its affinity for a transcytosis target, Sci. Transl. Med. 2011, 3, 84ra44.

Zhu et al., Immunology and Cell Biology (2010) 88:667-675.

Zuchero Y J et al. Discovery of Novel Blood-Brain Barrier Targets to Enhance Brain Uptake of Therapeutic Antibodies. Neuron, 89(1), 70-82 (2016).

WO/2004/076670

WO2003/046560

WO 2002/057445

WO 2011/127580

WO 2007/036021

The invention claimed is:

1. An isolated or purified antibody or fragment thereof, comprising the sequence $X_1$VQLVESGGGLVQPGGSLRLSCAASGFKITHYTMGWX$_2$RQAPGKX$_3$X$_4$EX$_5$VSRITWGGDNTFYSNSVKGRFTISRDNSKNTX$_6$YLQMNSLRAEDTAVYYCAAGSTSTATPLRVDYW GQGTLVTVSS (SEQ ID NO:9), where $X_1$=D or E, $X_2$=F or V, $X_3$=E or G, $X_4$=R or L, $X_5$=F or W, $X_6$=L or V.

2. The isolated or purified antibody or fragment thereof of claim 1, wherein the sequence is selected from any one of SEQ ID NOs: 2 to 8.

3. The isolated or purified antibody or fragment thereof of claim 1, wherein the antibody or fragment thereof is in a multivalent display format.

4. The isolated or purified antibody or fragment thereof of claim 3, wherein the antibody or fragment thereof is linked to a Fc fragment.

5. The isolated or purified antibody or fragment thereof of claim 4, wherein the Fc fragment is the mouse Fc2b or human Fc1.

6. The isolated or purified antibody or fragment thereof of claim 5, wherein the Fc comprises the sequence of SEQ ID NO:20.

7. The isolated or purified antibody or fragment thereof of claim 1, wherein the isolated or purified antibody or fragment thereof transmigrates the blood-brain barrier.

8. The isolated or purified antibody or fragment thereof of claim 1, wherein the antibody or fragment thereof is immobilized onto a surface.

9. The isolated or purified antibody or fragment thereof of claim 1, wherein the antibody or fragment thereof is linked to a cargo molecule.

10. The isolated or purified antibody or fragment thereof of claim 9, wherein the cargo molecule has a molecular weight in the range of about 1 kDa to about 200 kDa.

11. The isolated or purified antibody or fragment thereof of claim 9, wherein the cargo molecule is a detectable agent, a therapeutic, a drug, a peptide, a growth factor, a cytokine, a receptor trap, a chemical compound, a carbohydrate moiety, an enzyme, an antibody or fragment thereof, a DNA-based molecule, a viral vector, or a cytotoxic agent; one or more liposomes or nanocarriers loaded with a detectable agent, a therapeutic, a drug, a peptide, an enzyme, an antibody or fragment thereof, a DNA-based molecule, a viral vector, or a cytotoxic agent; or one or more nanoparticle, nanowire, nanotube, or quantum dots.

12. A composition comprising one or more than one isolated or purified antibody or fragment thereof of claim 1 and a pharmaceutically-acceptable carrier, diluent, or excipient.

13. A nucleic acid molecule encoding the isolated or purified antibody or fragment thereof of claim 1.

14. A vector comprising the nucleic acid molecule of claim 13.

* * * * *

SEQUENCE LISTING

```
<160> NUMBER OF SEQ ID NOS: 20

<210> SEQ ID NO 1
<211> LENGTH: 122
<212> TYPE: PRT
<213> ORGANISM: Artificial Sequence
<220> FEATURE:
<223> OTHER INFORMATION: FC5
```

-continued

<400> SEQUENCE: 1

```
Asp Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Gly Ser Thr Ser Thr Ala Thr Pro Leu Arg Val Asp Tyr Trp
            100                 105                 110

Gly Lys Gly Thr Gln Val Thr Val Ser Ser
        115                 120
```

<210> SEQ ID NO 2
<211> LENGTH: 122
<212> TYPE: PRT
<213> ORGANISM: Artificial Sequence
<220> FEATURE:
<223> OTHER INFORMATION: FC5-H1

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Val Arg Gln Ala Pro Gly Lys Gly Leu Glu Trp Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser
        115                 120
```

<210> SEQ ID NO 3
<211> LENGTH: 122
<212> TYPE: PRT
<213> ORGANISM: Artificial Sequence
<220> FEATURE:
<223> OTHER INFORMATION: FC5-H2

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Val Arg Gln Ala Pro Gly Lys Gly Leu Glu Trp Val
        35                  40                  45
```

```
Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser
        115                 120


<210> SEQ ID NO 4
<211> LENGTH: 122
<212> TYPE: PRT
<213> ORGANISM: Artificial Sequence
<220> FEATURE:
<223> OTHER INFORMATION: FC5-H3

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Gly Leu Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser
        115                 120


<210> SEQ ID NO 5
<211> LENGTH: 122
<212> TYPE: PRT
<213> ORGANISM: Artificial Sequence
<220> FEATURE:
<223> OTHER INFORMATION: FC5-H4

<400> SEQUENCE: 5

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Gly Leu Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
```

```
            100                 105                 110

Gly Gln Gly Thr Leu Val Thr Val Ser Ser
        115                 120


<210> SEQ ID NO 6
<211> LENGTH: 122
<212> TYPE: PRT
<213> ORGANISM: Artificial Sequence
<220> FEATURE:
<223> OTHER INFORMATION: FC5-H5

<400> SEQUENCE: 6

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Gly Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser
        115                 120


<210> SEQ ID NO 7
<211> LENGTH: 122
<212> TYPE: PRT
<213> ORGANISM: Artificial Sequence
<220> FEATURE:
<223> OTHER INFORMATION: FC5-H6

<400> SEQUENCE: 7

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser
        115                 120


<210> SEQ ID NO 8
<211> LENGTH: 122
<212> TYPE: PRT
<213> ORGANISM: Artificial Sequence
<220> FEATURE:
```

<223> OTHER INFORMATION: FC5-H7

<400> SEQUENCE: 8

Glu Val Gln Leu Val Glu Ser Gly Gly Gly Leu Val Gln Pro Gly Gly
1 5 10 15

Ser Leu Arg Leu Ser Cys Ala Ala Ser Gly Phe Lys Ile Thr His Tyr
20 25 30

Thr Met Gly Trp Phe Arg Gln Ala Pro Gly Lys Glu Arg Glu Phe Val
35 40 45

Ser Arg Ile Thr Trp Gly Gly Asp Asn Thr Phe Tyr Ser Asn Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ala Gly Ser Thr Ser Thr Ala Thr Pro Leu Arg Val Asp Tyr Trp
100 105 110

Gly Gln Gly Thr Leu Val Thr Val Ser Ser
115 120

<210> SEQ ID NO 9
<211> LENGTH: 123
<212> TYPE: PRT
<213> ORGANISM: Artificial Sequence
<220> FEATURE:
<223> OTHER INFORMATION: Humanized FC5 consensus sequence
<220> FEATURE:
<221> NAME/KEY: MISC_FEATURE
<222> LOCATION: (1)..(1)
<223> OTHER INFORMATION: X is Asp or Glu
<220> FEATURE:
<221> NAME/KEY: MISC_FEATURE
<222> LOCATION: (37)..(37)
<223> OTHER INFORMATION: X is Phe or Val
<220> FEATURE:
<221> NAME/KEY: MISC_FEATURE
<222> LOCATION: (44)..(44)
<223> OTHER INFORMATION: X is Glu or Gly
<220> FEATURE:
<221> NAME/KEY: MISC_FEATURE
<222> LOCATION: (45)..(45)
<223> OTHER INFORMATION: X is Arg or Leu
<220> FEATURE:
<221> NAME/KEY: MISC_FEATURE
<222> LOCATION: (47)..(47)
<223> OTHER INFORMATION: X is Phe or Trp
<220> FEATURE:
<221> NAME/KEY: MISC_FEATURE
<222> LOCATION: (79)..(79)
<223> OTHER INFORMATION: X is Leu or Val

<400> SEQUENCE: 9

Xaa Val Gln Leu Val Glu Ser Gly Gly Gly Leu Val Gln Pro Gly Gly
1 5 10 15

Ser Leu Arg Leu Ser Cys Ala Ala Ser Gly Phe Lys Ile Thr His Tyr
20 25 30

Thr Met Gly Trp Xaa Arg Gln Ala Pro Gly Lys Xaa Xaa Glu Xaa Val
35 40 45

Ser Arg Ile Thr Trp Gly Gly Asp Asn Thr Phe Tyr Ser Asn Ser Val
50 55 60

Lys Gly Arg Phe Thr Ile Ser Arg Asp Asn Ser Lys Asn Thr Xaa Tyr
65 70 75 80

Leu Gln Met Asn Ser Leu Arg Ala Glu Asp Thr Ala Val Tyr Tyr Cys
85 90 95

```
Ala Ala Gly Ser Thr Ser Thr Ala Thr Pro Leu Arg Val Asp Tyr Trp
            100                 105                 110

Gly Gln Gly Thr Leu Val Thr Val Ser Ser Val
        115                 120


<210> SEQ ID NO 10
<211> LENGTH: 30
<212> TYPE: PRT
<213> ORGANISM: Artificial Sequence
<220> FEATURE:
<223> OTHER INFORMATION: fdTGIII primer

<400> SEQUENCE: 10

Gly Thr Gly Ala Ala Ala Ala Ala Ala Thr Thr Ala Thr Thr Ala Thr
1               5                   10                  15

Thr Ala Thr Thr Cys Gly Cys Ala Ala Thr Thr Cys Cys Thr
            20                  25                  30


<210> SEQ ID NO 11
<211> LENGTH: 20
<212> TYPE: PRT
<213> ORGANISM: Artificial Sequence
<220> FEATURE:
<223> OTHER INFORMATION: 96GIII

<400> SEQUENCE: 11

Cys Cys Cys Thr Cys Ala Thr Ala Gly Thr Thr Ala Gly Cys Gly Thr
1               5                   10                  15

Ala Ala Cys Gly
            20


<210> SEQ ID NO 12
<211> LENGTH: 15
<212> TYPE: PRT
<213> ORGANISM: Artificial Sequence
<220> FEATURE:
<223> OTHER INFORMATION: Peptide for nano-LC-SRM

<400> SEQUENCE: 12

Ile Thr Trp Gly Gly Asp Asn Thr Phe Tyr Ser Asn Ser Val Lys
1               5                   10                  15


<210> SEQ ID NO 13
<211> LENGTH: 9
<212> TYPE: PRT
<213> ORGANISM: Artificial Sequence
<220> FEATURE:
<223> OTHER INFORMATION: Peptide for nano-LC-SRM

<400> SEQUENCE: 13

Thr Thr Tyr Tyr Ala Asp Ser Val Lys
1               5


<210> SEQ ID NO 14
<211> LENGTH: 11
<212> TYPE: PRT
<213> ORGANISM: Artificial Sequence
<220> FEATURE:
<223> OTHER INFORMATION: Peptide for nano-LC-SRM

<400> SEQUENCE: 14

Glu Phe Val Ala Ala Gly Ser Ser Thr Gly Arg
1               5                   10
```

<210> SEQ ID NO 15
<211> LENGTH: 11
<212> TYPE: PRT
<213> ORGANISM: Artificial Sequence
<220> FEATURE:
<223> OTHER INFORMATION: Peptide for nano-LC-SRM

<400> SEQUENCE: 15

Thr Phe Ser Met Asp Pro Met Ala Trp Phe Arg
1               5                   10

<210> SEQ ID NO 16
<211> LENGTH: 26
<212> TYPE: PRT
<213> ORGANISM: Artificial Sequence
<220> FEATURE:
<223> OTHER INFORMATION: Peptide for nano-LC-SRM

<400> SEQUENCE: 16

Asp Glu Tyr Ala Tyr Trp Gly Gln Gly Thr Gln Val Thr Val Ser Ser
1               5                   10                  15

Gly Gln Ala Gly Gln Gly Ser Glu Gln Lys
            20                  25

<210> SEQ ID NO 17
<211> LENGTH: 9
<212> TYPE: PRT
<213> ORGANISM: Artificial Sequence
<220> FEATURE:
<223> OTHER INFORMATION: Peptide for nano-LC-SRM

<400> SEQUENCE: 17

Leu Ser Cys Ala Ala Ser Gly Phe Lys
1               5

<210> SEQ ID NO 18
<211> LENGTH: 11
<212> TYPE: PRT
<213> ORGANISM: Artificial Sequence
<220> FEATURE:
<223> OTHER INFORMATION: Peptide for nano-LC-SRM

<400> SEQUENCE: 18

Asn Thr Leu Tyr Leu Gln Met Asn Ser Leu Arg
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Peptide for nano-LC-SRM

<400> SEQUENCE: 19

Leu Ser Cys Ala Ala Ser Gly Phe Lys
1               5

<210> SEQ ID NO 20
<211> LENGTH: 232
<212> TYPE: PRT
<213> ORGANISM: Artificial Sequence
<220> FEATURE:
<223> OTHER INFORMATION: IgG1 Fc

<400> SEQUENCE: 20

Ala Glu Pro Lys Ser Cys Asp Lys Thr His Thr Cys Pro Pro Cys Pro
1               5                   10                  15

-continued

```
Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Gly Pro Glu Val Lys Phe Asn Trp His
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Gly Leu His Asn His Tyr Thr Gln
    210                 215                 220

Lys Ser Leu Ser Leu Ser Pro Gly
225                 230
```